United States Patent
Mujwid et al.

(10) Patent No.: US 11,311,382 B2
(45) Date of Patent: Apr. 26, 2022

(54) PUMP ASSEMBLY HAVING A PUSH VALVE FOR A PENILE PROSTHESIS

(71) Applicant: Boston Scientific Scimed, Inc., Maple Grove, MN (US)

(72) Inventors: James Ryan Mujwid, Hudson, WI (US); Ryan Earl Fredrick, Eden Prairie, MN (US); Mark Edward DiLoreto, Chaska, MN (US); John Anders Bostrom, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 156 days.

(21) Appl. No.: 16/687,073

(22) Filed: Nov. 18, 2019

(65) Prior Publication Data

US 2020/0163770 A1     May 28, 2020

Related U.S. Application Data

(60) Provisional application No. 62/771,874, filed on Nov. 27, 2018.

(51) Int. Cl.
*A61F 2/26*         (2006.01)

(52) U.S. Cl.
CPC ........ *A61F 2/26* (2013.01); *A61F 2250/0013* (2013.01)

(58) Field of Classification Search
CPC ....................................................... A61F 2/26
See application file for complete search history.

(56) References Cited

U.S. PATENT DOCUMENTS

| 4,566,446 A | 1/1986 | Fogarty et al. |
| 6,003,906 A | 12/1999 | Fogarty et al. |
| 6,171,233 B1 | 1/2001 | Willard et al. |
| 6,443,887 B1 | 9/2002 | Derus et al. |

(Continued)

FOREIGN PATENT DOCUMENTS

| EP | 1255513 B1 | 5/2005 |
| EP | 1670393 B1 | 9/2009 |

(Continued)

OTHER PUBLICATIONS

International Search Report and Written Opinion for Application No. PCT/US2019/062213, dated Mar. 23, 2020, 12 pages.

*Primary Examiner* — John P Lacyk
(74) *Attorney, Agent, or Firm* — Brake Hughes Bellermann LLP

(57) ABSTRACT

According to an aspect, an inflatable penile prosthesis includes a fluid reservoir, an inflatable member, and a pump assembly. The pump assembly includes a pump bulb, a valve body, a push valve movably coupled to the valve body, a first fluid port, and a second fluid port. The push valve includes a movable valve element configured to move between an inflation position and a deflation position within a bore of the valve body. The movable valve element in the inflation position defines a fluid passageway through the bore to transfer fluid from the pump bulb to the second fluid port. The movable valve element, when moved to the deflation position, is configured to change the fluid passageway through the bore to transfer fluid from the second fluid port to the first fluid port such that the pump bulb is bypassed.

20 Claims, 21 Drawing Sheets

(56) References Cited

U.S. PATENT DOCUMENTS

| | | | |
|---|---|---|---|
| 6,533,719 | B2 | 3/2003 | Kuyava et al. |
| 6,558,315 | B1 | 5/2003 | Kuyava |
| 6,723,042 | B2 | 4/2004 | Almli et al. |
| 6,730,017 | B2 | 5/2004 | Kuyava et al. |
| 6,808,489 | B2 | 10/2004 | George et al. |
| 6,808,490 | B1 | 10/2004 | Ling et al. |
| 6,929,599 | B2 | 8/2005 | Westrum |
| 6,935,847 | B2 | 8/2005 | Kuyava et al. |
| 6,991,601 | B2 | 1/2006 | Kuyava et al. |
| 6,991,604 | B2 | 1/2006 | Cantrell |
| 6,997,919 | B2 | 2/2006 | Olsen et al. |
| 7,169,103 | B2 | 1/2007 | Ling et al. |
| 7,244,227 | B2 | 7/2007 | Morningstar et al. |
| 7,250,026 | B2 | 7/2007 | Kuyava et al. |
| 7,350,538 | B2 | 4/2008 | Kuyava et al. |
| 7,390,296 | B2 | 6/2008 | Mische |
| 7,407,482 | B2 | 8/2008 | Kuyava et al. |
| 7,438,682 | B2 | 10/2008 | Kuyava et al. |
| 7,442,165 | B2 | 10/2008 | Forsell |
| 7,637,861 | B2 | 12/2009 | Kuyava et al. |
| 7,717,845 | B2 | 5/2010 | George et al. |
| 7,874,978 | B2 | 1/2011 | Kuyava et al. |
| 7,914,439 | B2 | 3/2011 | Kuyava et al. |
| 7,946,975 | B2 | 5/2011 | George et al. |
| 7,963,909 | B2 | 6/2011 | George et al. |
| 8,016,746 | B2 | 9/2011 | Ellering |
| 8,062,209 | B2 | 11/2011 | Rowland et al. |
| 8,109,870 | B2 | 2/2012 | Kuyava et al. |
| 8,167,788 | B2 | 5/2012 | Arp et al. |
| 8,241,203 | B2 | 8/2012 | Fogarty |
| 8,257,246 | B1 * | 9/2012 | Fogarty .................. A61F 2/26 600/40 |
| 8,276,591 | B2 | 10/2012 | Henkel et al. |
| 8,337,392 | B2 * | 12/2012 | Morningstar ............ A61F 2/26 600/40 |
| 8,348,826 | B2 | 1/2013 | Gomez-Llorens |
| 8,491,462 | B2 | 7/2013 | Chechik |
| 8,517,916 | B2 | 8/2013 | Ellering |
| 8,523,761 | B2 | 9/2013 | Ellering |
| 8,545,393 | B2 | 10/2013 | Ellering |
| 8,568,294 | B2 | 10/2013 | Ellering |
| 8,617,052 | B2 | 12/2013 | Fogarty |
| 8,632,456 | B2 | 1/2014 | Fogarty et al. |
| 8,641,601 | B2 | 2/2014 | Ellering |
| 8,684,910 | B2 | 4/2014 | Chechik |
| 8,740,769 | B2 | 6/2014 | Chechik |
| 8,740,771 | B2 | 6/2014 | Ellering |
| 8,801,594 | B2 | 8/2014 | Fogarty |
| 8,932,203 | B2 | 1/2015 | Ellering |
| 8,932,204 | B2 | 1/2015 | Fogarty et al. |
| 8,939,889 | B1 | 1/2015 | Chechik |
| 8,939,890 | B2 | 1/2015 | Morningstar |
| 8,951,186 | B2 | 2/2015 | Ellering |
| D725,271 | S | 3/2015 | Chechik |
| 8,974,370 | B2 | 3/2015 | Chechik |
| 9,017,245 | B2 | 4/2015 | Forsell |
| 9,089,426 | B2 | 7/2015 | Henkel et al. |
| 9,101,474 | B2 | 8/2015 | Derus |
| 9,186,251 | B2 | 11/2015 | Fogarty et al. |
| 9,241,824 | B2 | 1/2016 | Ellering |
| 9,308,088 | B2 | 4/2016 | Chechik |
| 9,554,937 | B2 | 1/2017 | Daniel |
| 9,561,107 | B2 | 2/2017 | Daniel |
| 9,566,155 | B2 | 2/2017 | Chechik |
| 9,649,217 | B2 | 5/2017 | Daniel |
| 9,795,484 | B2 | 10/2017 | Daniel |
| 9,814,554 | B2 | 11/2017 | McClurg |
| 9,861,481 | B2 | 1/2018 | Daniel |
| 9,877,834 | B2 | 1/2018 | Vaingas et al. |
| 9,907,653 | B2 | 3/2018 | Taylor |
| 9,956,079 | B2 | 5/2018 | Daniel |
| 9,987,136 | B2 | 6/2018 | Daniel |
| 9,999,508 | B2 | 6/2018 | Darnell et al. |
| 10,098,741 | B2 | 10/2018 | Wolf |
| 10,285,815 | B2 | 5/2019 | Henkel et al. |
| 10,327,902 | B2 | 6/2019 | Forsell |
| 10,383,730 | B2 | 8/2019 | Daniel |
| 10,682,233 | B2 | 6/2020 | Wolf |
| 10,722,367 | B2 | 7/2020 | Kansas et al. |
| 10,729,547 | B2 | 8/2020 | Darnell et al. |
| 2007/0142700 | A1 | 6/2007 | Fogarty et al. |
| 2013/0072751 | A1 | 3/2013 | Fogarty |
| 2016/0120649 | A1 | 5/2016 | Vaingast et al. |
| 2017/0209271 | A1 | 7/2017 | Daniel |
| 2018/0214271 | A1 | 8/2018 | Poucher et al. |
| 2018/0214272 | A1 | 8/2018 | Elist |
| 2018/0289489 | A1 | 10/2018 | Hakky |
| 2019/0000626 | A1 | 1/2019 | Tal et al. |
| 2020/0146827 | A1 | 5/2020 | Allen et al. |
| 2020/0155319 | A1 | 5/2020 | Allen et al. |

FOREIGN PATENT DOCUMENTS

| | | |
|---|---|---|
| EP | 2272465 A1 | 1/2011 |
| EP | 2391302 A1 | 12/2011 |
| EP | 2391307 A1 | 12/2011 |
| EP | 2531144 B1 | 6/2014 |
| EP | 2767261 A1 | 8/2014 |
| EP | 2805689 A1 | 11/2014 |
| EP | 2839809 A1 | 2/2015 |
| EP | 1962745 B1 | 9/2015 |
| EP | 2501339 B1 | 2/2016 |
| EP | 2741712 B1 | 6/2016 |
| EP | 2957263 B1 | 9/2016 |
| EP | 2965719 B1 | 10/2016 |
| EP | 3123981 A1 | 2/2017 |
| EP | 3135250 A1 | 3/2017 |
| EP | 2747710 B1 | 4/2017 |
| EP | 3150175 A1 | 4/2017 |
| EP | 3222249 A1 | 9/2017 |
| EP | 3242631 A1 | 11/2017 |
| EP | 2696808 B1 | 7/2018 |
| EP | 2415422 B1 | 8/2018 |
| EP | 3384875 A1 | 10/2018 |
| EP | 3393402 A1 | 10/2018 |
| EP | 3100702 B1 | 12/2018 |
| EP | 3028673 B1 | 7/2019 |
| EP | 3001980 B1 | 11/2019 |
| EP | 3563807 A1 | 11/2019 |
| EP | 3574870 A1 | 12/2019 |
| KR | 101131148 B1 | 3/2012 |
| WO | 2013020555 A2 | 2/2013 |
| WO | 2014123408 A1 | 8/2014 |
| WO | 2021029834 A1 | 2/2021 |

* cited by examiner

PUMP ASSEMBLY HAVING A PUSH VALVE FOR A PENILE PROSTHESIS

CROSS-REFERENCE TO RELATED APPLICATION

This application is a Nonprovisional of, and claims priority to, U.S. Patent Application No. 62/771,874, filed on Nov. 27, 2018, entitled "PUMP ASSEMBLY HAVING A PUSH VALVE FOR A PENILE PROSTHESIS", which is incorporated by reference herein in its entirety.

TECHNICAL FIELD

This disclosure relates generally to bodily implants and more specifically to bodily implants, such as a penile prosthesis that includes a pump assembly having a push valve to switch to a deflation mode.

BACKGROUND

One treatment for male erectile dysfunction is the implantation of a penile prosthesis that mechanically erects the penis. Some existing penile prostheses include inflatable cylinders or members that can be inflated or deflated using a pump mechanism. The pump mechanism pulls fluid from a fluid reservoir and then transfers the fluid to the inflatable members. The pump mechanism may include a pump bulb and a valve body that includes one or more valve components. According to some existing designs of inflatable penile prostheses, the complexity of the valve components may cause the pump bulb to get struck in a collapsed state, where the user may have to deform the valve block in order to dislodge one or more valve components until fluid is able to pass around them to refill the pump bulb.

SUMMARY

According to an aspect, an inflatable penile prosthesis includes a fluid reservoir configured to hold fluid, an inflatable member, and a pump assembly configured to transfer the fluid between the fluid reservoir and the inflatable member. The pump assembly includes a pump bulb, a valve body, a push valve movably coupled to the valve body, a first fluid port configured to be fluidly coupled to the fluid reservoir, and a second fluid port configured to be fluidly coupled to the fluid reservoir. The push valve includes a movable valve element configured to move between an inflation position and a deflation position within a bore of the valve body. The movable valve element in the inflation position defines a fluid passageway through the bore to transfer fluid from the pump bulb to the second fluid port. The movable valve element, when moved to the deflation position, is configured to change the fluid passageway through the bore to transfer fluid from the second fluid port to the first fluid port such that the pump bulb is bypassed.

According to some aspects, the inflatable penile prosthesis may include one or more of the following features (or any combination thereof). The push valve may include a biasing member that biases the movable valve element to the inflation position. The push valve may include a poppet having a ring member. The movable valve element is configured to move to the deflation position in a linear direction based on a single instantaneous push of the movable valve element by a user. The pump assembly may include a button component that encloses a portion of the movable valve element when the movable valve element is in the inflation position. The pump assembly may include a feedback component disposed between the button component and the movable valve element, where the feedback component is configured to provide at least one of tactile or auditory feedback in response to the movable valve element being moved to the deflation position. A portion of the movable valve element may extend outside the valve body when the movable valve element is in the inflation position, and the portion of the movable valve element may be disposed inside the valve body when the movable valve element is in the deflation position. The valve body may include a refill valve aligned with the first fluid port, and the refill valve is configured to transfer fluid from the fluid reservoir to the pump bulb when the movable valve element is in the inflation position. The valve body may include an inflation valve disposed in a fluid passageway between the pump bulb and the bore. The movable valve element may include a first movable member and a second movable member, where the first movable member and the second movable member are configured to independently move with respect to each other. The valve body may include a refill valve, and an inflation valve, where the refill valve and the inflation valve are not used when the movable valve element is in the deflation position.

According to an aspect, a pump assembly for an inflatable penile prosthesis includes a push valve movably coupled to a valve body, where the push valve includes a movable valve element configured to move between an inflation position and a deflation position within a bore of the valve body, and a plurality of fluid transfer ports including a first fluid port configured to be fluidly coupled to a fluid reservoir, and a second fluid port configured to be fluidly coupled to an inflatable member. The movable valve element in the inflation position defines a fluid passageway through the bore to transfer fluid from a pump bulb to the second fluid port. The movable valve element, when moved to the deflation position, is configured to change the fluid passageway through the bore to transfer fluid from the second fluid port to the first fluid port such that the pump bulb is bypassed.

According to some aspects, the pump assembly may include any of the above/below features (or any combination thereof). The movable valve element may include a cylindrical unitary body having at least two sections with different diameters. The first fluid port includes a first tubular member, and the second fluid port includes a second tubular member and a third tubular member. The second tubular member is configured to be fluidly coupled to a first cylinder member of the inflatable member, and the third tubular member is configured to be fluidly coupled to a second cylinder member of the inflatable member. The pump assembly includes a refill valve disposed within the valve body at a location that is aligned with a longitudinal axis of the first fluid port, and an inflation valve disposed in a fluid passageway between the bore and the pump bulb. The movable valve element is configured to move from the inflation position to the deflation position along an axis, where the axis is substantially orthogonal to the longitudinal axis of the first fluid port. The pump assembly may include an anti-auto inflate valve disposed in a fluid passageway between the first fluid port and the second fluid port. A portion of the movable valve element may extend outside the valve body when the movable valve element is in the inflation position, and the pump assembly may further include a button component that encloses the portion of the movable valve element, and a feedback component disposed between the button component and an end portion of the movable valve element. The feedback component is configured to provide at least one of tactile or auditory feedback in response to the movable valve element being moved to the deflation position.

According to an aspect, a method for controlling a direction of fluid through a pump assembly of an inflatable penile prosthesis includes transferring, by a pump assembly, fluid from a fluid reservoir to an inflatable member, including transferring the fluid from the fluid reservoir to a pump bulb via a refill valve, and transferring the fluid from the pump bulb to the inflatable member via an inflation valve and a push valve having a movable valve element. The method includes pushing the movable valve element along an axis to a deflation position to change a fluid passageway through a valve body of the pump assembly, and transferring the fluid from the inflatable member to the fluid reservoir via the push valve such that the fluid is not transferred through the pump bulb. In some examples, the refill valve and the inflation valve are not used to transfer the fluid from the inflation member to the fluid reservoir when the movable valve element is in the deflation position.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the embodiments are directed to bodily implants. The term patient or user may hereafter be used for a person who benefits from the medical device or the methods disclosed in the present disclosure. For example, the patient can be a person whose body is implanted with the medical device or the method disclosed for operating the medical device by the present disclosure.

Figure 1:
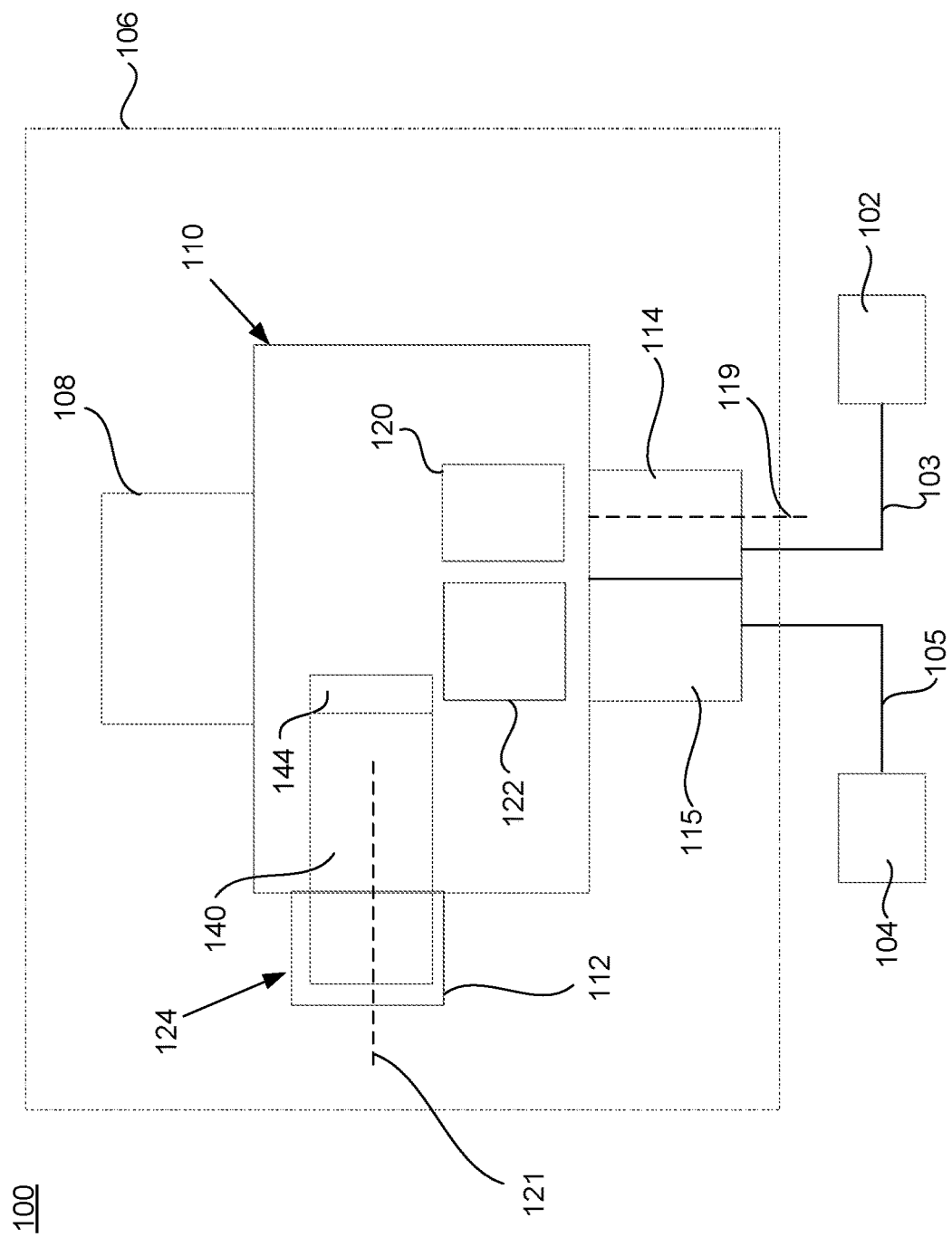
FIG. 1 illustrates an inflatable penile prosthesis having a pump assembly with a push valve according to an aspect.

FIG. 1 illustrates an inflatable penile prosthesis 100 including a fluid reservoir 102, an inflatable member 104, and a pump assembly 106 configured to transfer fluid between the fluid reservoir 102 and the inflatable member 104 according to an aspect. The inflatable member 104 may be implanted into the corpus cavernosae of the user, the fluid reservoir 102 may be implanted in the abdomen or pelvic cavity of the user (e.g., the fluid reservoir 102 may be implanted in the lower portion of the user's abdominal cavity or the upper portion of the user's pelvic cavity), and the pump assembly 106 may be implanted in the scrotum of the user.

The pump assembly 106 includes a pump bulb 108, a valve body 110, a push valve 124 movably coupled to the valve body 110, a first fluid port 114 fluidly coupled to the fluid reservoir 102 (via a first conduit connector 103), and a second fluid port 115 fluidly coupled to the inflatable member 104 (via a second conduit connector 105). The first fluid port 114 and the second fluid port 115 may extend from an end portion of the valve body 110. In some examples, the fluid transfer ports are disposed on (or defined by) a tube adaptor (e.g., a triple tube adaptor) that is separate from the valve body 110, and the tube adaptor is coupled to the valve body 110. In some examples, the first fluid port 114 includes an elongated tubular member defining a cavity. In some examples, the second fluid port 115 includes two separate elongated tubular members (e.g., one tubular member being fluidly coupled to a first cylinder member of the inflatable member 104 and another tubular member being fluidly coupled to a second cylinder member of the inflatable member 104).

The push valve 124 is configured to move from an inflation position to a deflation position along an axis 121 within a bore of the valve body 110 when pressed by a user in order to control the direction of the fluid through the fluid passageways of the valve body 110. The push valve 124 includes a movable valve element 140 and a biasing member 144 that biases the movable valve element 140 to the inflation position. In some examples, the movable valve element 140 is configured to move to the deflation position in a linear direction based on a single instantaneous push of the movable valve element 140 by a user. The pump assembly 106 includes a button component 112 that encloses a portion of the movable valve element 140 when the movable valve element 140 is in the inflation position. The button component 112 may be a flexible button-shaped material that extends over the movable valve element 140.

In some examples, the movable valve element 140 includes a directional control valve. In some examples, the movable valve element 140 includes an elongated cylindrical body having at least two sections with different sizes. In some examples, the movable valve element 140 includes one or more ring members (e.g., annular rings or retainer rings). In some examples, the biasing member 144 includes a spring. In some examples, the movable valve element 140 includes a single unitary body (e.g., a single cylindrical member). In some examples, the movable valve element 140 includes a two-piece member (e.g., first and second movable members that are concentrically aligned and move independently of each other).

The design of the push valve 124 may reduce (or eliminate) the possibility for the pump bulb 108 to get stuck in a collapsed state even if the first squeeze to switch from the deflation mode to the inflation mode does not successfully move the movable valve element 140 to the inflation position. When the movable valve element 140 is in the inflation position, the inflatable penile prosthesis 100 is in an inflation mode (or inflation cycle). When the movable valve element 140 is in the deflation position, the inflatable penile prosthesis 100 is in a deflation mode (or deflation cycle). In some examples, a single, instantaneous push of the movable valve element 140 transfers the inflatable penile prosthesis 100 to the deflation position (e.g., as opposed to pressing and holding the movable valve element 140 for a certain predetermined time). In some examples, movement of the movable valve element 140 to the deflation position causes a fluid pathway to open between the second fluid port 115 and the first fluid port 114 such that fluid can be transferred from the inflatable member 104 to the fluid reservoir 102 via the pump assembly 106 in a manner that bypasses the pump bulb 108.

In contrast, in the inflation mode, the pump bulb 108 is used to transfer fluid from the fluid reservoir 102 to the inflatable member 104. For example, the user may depress (or squeeze) the pump bulb 108 and then release the pump bulb 108, and then repeat these operations until the desired rigidity is achieved in the inflatable member 104. The release of the pump bulb 108 creates a suction force that pulls fluid from the fluid reservoir 102 to the pump bulb 108, and the depression of the pump bulb 108 expels the fluid from the pump bulb 108 to the inflatable member 104. In some examples, in the inflation mode, the valve body 110 provides an optimized fluid passageway via the push valve 124 that may decrease the pressure drop across the push valve 124 for faster inflate time and/or decrease the fluid resistance thereby requiring less pump bulb squeeze force to inflate.

The pump bulb 108 may be a flexible member defining a cavity. The pump bulb 108 is coupled to and extends from the valve body 110. In some examples, the pump bulb 108 extends from the valve body 110 in a direction that is opposite to the direction in which the first fluid port 114 and the second fluid port 115 extend from the valve body 110 (e.g., located on opposite ends of the valve body 110). The pump bulb 108 may be a squeeze pump. In some examples, the pump bulb 108 includes ribbing or dimples to aid the user in gripping the pump bulb 108. As indicated above, the pump bulb 108 may use suction and pressure to move the fluid in and out of the cavity of the pump bulb 108 in the inflation mode. For example, the user may depress or squeeze the pump bulb 108 to expel the fluid out of the cavity, and, when the flexible member returns to its original shape, the resulting suction pushes the fluid into the cavity of the pump bulb 108. In some examples, the pump bulb 108 may have a bulb spring rate that is designed to refill the pump bulb 108 in a selected time frame.

The valve body 110 defines one or more fluid passageways through the valve body 110. The valve body 110 includes valve components disposed within the fluid passageways to control the flow of the fluid through the valve body 110 in the inflation mode and the deflation mode. In some examples, the valve body 110 includes a block of material that defines the fluid passageways and encloses the valve components. In some examples, the valve body 110 includes a silicone material. In some examples, the valve body 110 may be molded from a silicone material having a medium durometer value. In some examples, the pump assembly 106 includes an outer protective casing that is disposed over the valve body 110. In some examples, the outer protective casing has a material (e.g., a polymer material) that is different from the valve body 110. In some examples, the outer protective casing includes one or more tactile features that help the user locate the valve body 110 (in order to locate the push valve 124). In some examples, the tactile features include protruded portions, ridges, grooves, bumps, and/or depressions.

The valve body 110 includes a refill valve 120 and an inflation valve 122. In some examples, the valve body 110 includes an anti-auto inflate valve. The refill valve 120 may be used when the pump bulb 108 is refilled. The refill valve 120 is not used in the deflation mode. In some examples, the refill valve 120 is a one-way valve. In some examples, the refill valve 120 is disposed in a fluid passageway within the valve body 110 between the first fluid port 114 and the pump bulb 108. In some examples, the fluid passageway having the refill valve 120 that extends between the first fluid port 114 and the pump bulb 108 is used only for refilling the pump bulb 108 (e.g., a separated fluid pathway), which may decrease bulb refill time (e.g., deceases the wait time between squeezes). In some examples, the refill valve 120 is fluidly coupled to the bore (where the push valve 124 moves within) and the pump bulb 108.

In some examples, the refill valve 120 is aligned with the first fluid port 114. For example, the refill valve 120 may have an inlet and an outlet, where fluid enters the inlet from the first fluid port 114 and exits the outlet to the pump bulb 108. The first fluid port 114 may define a longitudinal axis 119 that extends along the fluid pathway (e.g., between the inlet and the outlet) of the refill valve 120. In some examples, the longitudinal axis 119 is orthogonal to the axis 121. The alignment of the refill valve 120 with the first fluid port 114 may minimize fluid pathway tortuosity, and/or decrease pressure drop across the refill valve 120. In some examples, the refill valve 120 includes a floating check ball with fluting (which may increase or maximize fluid velocity across the refill valve 120). In some examples, the refill valve 120 includes a biasing member that biases the refill valve 120 to a sealing position. In some examples, the biasing member includes a spring. In some examples, the refill valve 120 does not include a biasing member.

The inflation valve 122 may be disposed within a fluid passageway between the pump bulb 108 and the push valve 124. The inflation valve 122 may be used during the inflation of the inflatable member 104 (e.g., when the fluid is transferred from the pump bulb 108 to the inflatable member 104). The inflation valve 122 is not used during the deflation mode. In some examples, the inflation valve 122 is a one-way valve. In some examples, the inflation valve 122 includes a check ball and a biasing member. The biasing member may bias the check ball to a sealing position. In some examples, the biasing member includes a spring.

In the inflation position (and when the user is operating the pump bulb 108), the fluid may flow from the first fluid port 114 (from the fluid reservoir 102) to the pump bulb 108 via the refill valve 120, and from the pump bulb 108 to the second fluid port 115 via the inflation valve 122 and the push valve 124 (and then to the inflatable member 104). In response to the movable valve element 140 being pressed to the deflation position, the position in the movable valve element 140 within the bore of the valve body 110 may open a fluid passageway in the valve body 110 to transfer fluid from the inflatable member 104 to the fluid reservoir 102 that bypasses the pump bulb 108. For example, the movable valve element 140, when moved to the deflation position, is configured to change the fluid passageway through the bore to transfer fluid from the second fluid port 115 to the first fluid port 114 such that the pump bulb 108 is bypassed. In some examples, due to the pressure inside of the inflatable member 104, some of the fluid may be automatically transferred from the inflation member 104 to the fluid reservoir 102 via the pump assembly 106, and then the user may squeeze the inflatable member 104 to transfer some of the remaining fluid in the inflatable member 104.

In some examples, the pump assembly 106 includes a feedback component disposed between the button component 112 and the movable valve element 140. The feedback component is configured to provide at least one of tactile or auditory feedback in response to the activation of the movable valve element 140 being moved to the deflation position. For example, when the movable valve element 140 is pressed, the feedback component may provide a sound and/or tactile feeling that the inflatable penile prosthesis 100 has entered the deflation mode. In some examples, the feedback component includes a dome component.

Each of the first conduit connector 103 and the second conduit connector 105 may define a lumen configured to transfer the fluid to and from the pump assembly 106. The first conduit connector 103 may be coupled to the pump assembly 106 and the fluid reservoir 102 such that fluid can be transferred between the pump assembly 106 and the fluid reservoir 102 via the first conduit connector 103. For example, the first conduit connector 103 may define a first lumen configured to transfer fluid between the pump assembly 106 and the fluid reservoir 102. The first conduit connector 103 may include a single or multiple tube members for transferring the fluid between the pump assembly 106 and the fluid reservoir 102.

The second conduit connector 105 may be coupled to the pump assembly 106 and the inflatable member 104 such that fluid can be transferred between the pump assembly 106 and the inflatable member 104 via the second conduit connector 105. For example, the second conduit connector 105 may define a second lumen configured to transfer fluid between the pump assembly 106 and the inflatable member 104. The second conduit connector 105 may include a single or multiple tube members for transferring the fluid between the pump assembly 106 and the inflatable member 104. In some examples, the first conduit connector 103 and the second conduit connector 105 may include a silicone rubber material. In some examples, the pump assembly 106 may be directly connected to the fluid reservoir 102.

The inflatable member 104 may be capable of expanding upon the injection of fluid into a cavity of the inflatable member 104. For instance, upon injection of the fluid into the inflatable member 104, the inflatable member 104 may increase its length and/or width, as well as increase its rigidity. In some examples, the inflatable member 104 may include a pair of inflatable cylinders or at least two cylinders, e.g., a first cylinder member and a second cylinder member. The volumetric capacity of the inflatable member 104 may depend on the size of the inflatable cylinders. In some examples, the volume of fluid in each cylinder may vary from about 10 milliliters in smaller cylinders and to about 50 milliliters in larger sizes. In some examples, the first cylinder member may be larger than the second cylinder member. In other examples, the first cylinder member may have the same size as the second cylinder member.

The fluid reservoir 102 may include a container having an internal chamber configured to hold or house fluid that is used to inflate the inflatable member 104. The volumetric capacity of the fluid reservoir 102 may vary depending on the size of the inflatable penile prosthesis 100. In some examples, the volumetric capacity of the fluid reservoir 102 may be 3 to 150 cubic centimeters. In some examples, the fluid reservoir 102 is constructed from the same material as the inflatable member 104. In other examples, the fluid reservoir 102 is constructed from a different material than the inflatable member 104. In some examples, the fluid reservoir 102 contains a larger volume of fluid than the inflatable member 104.

FIGS. 2A through 2E illustrate various perspectives of a pump assembly 206 having a push valve 224 configured to move from an inflation position to a deflation position to open a fluid passageway that transfers fluid from an inflatable member to a fluid reservoir in a manner that bypasses a pump bulb 208. For example, a user may push the push valve 224 to place the penile prosthesis in a deflation mode. In the inflation position, the pump assembly 206 transfers fluid from the fluid reservoir to the inflatable member via the pump bulb 208. However, in the deflation position, the pump assembly 206 transfers fluid from the inflatable member to the fluid reservoir that bypasses the pump bulb 208. In some examples, the push valve 224 is a switching valve. In some examples, the pump assembly 206 is an example of the pump assembly 106 of FIG. 1, and may include any of the features discussed with reference to the inflatable penile prosthesis 100 of FIG. 1. Also, the pump assembly 106 of FIG. 1 may include any of the features with respect to the pump assembly 206 of FIGS. 2A though 2E.

Figure 2A:
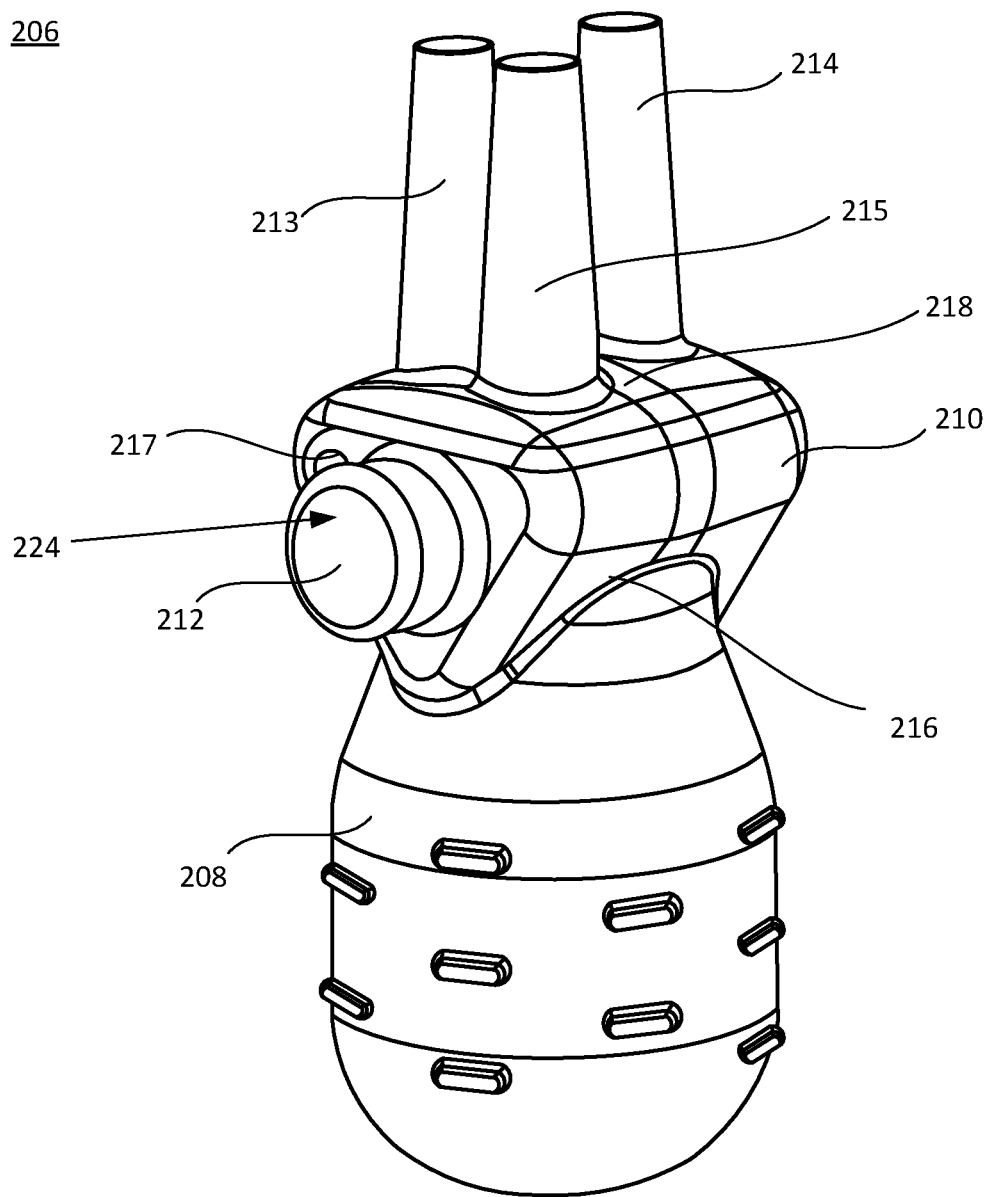
FIG. 2A illustrates an exterior of the pump assembly according to an aspect.
Figure 2B:
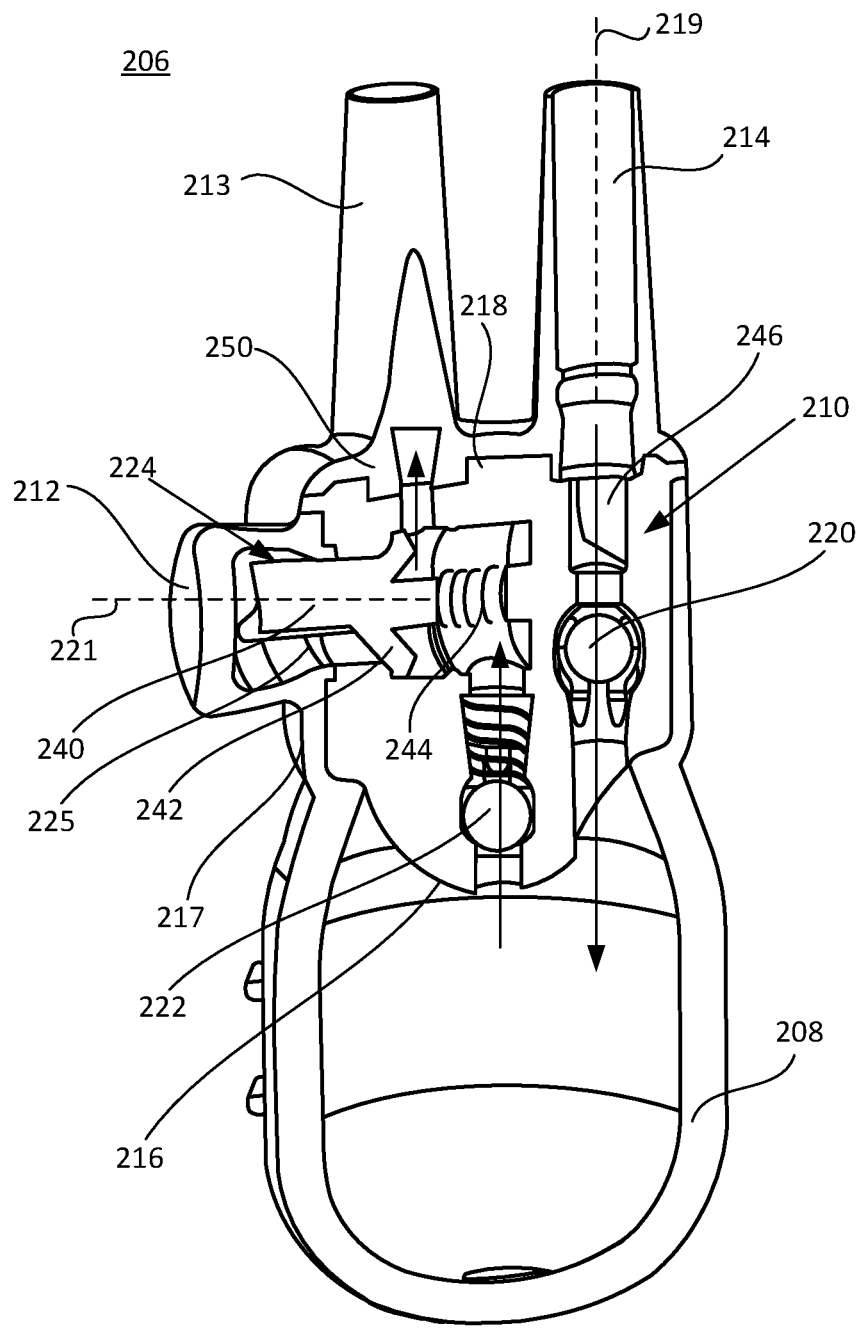
FIG. 2B illustrates a perspective of the pump assembly with the push valve in an inflation position according to an aspect.
Figure 2C:
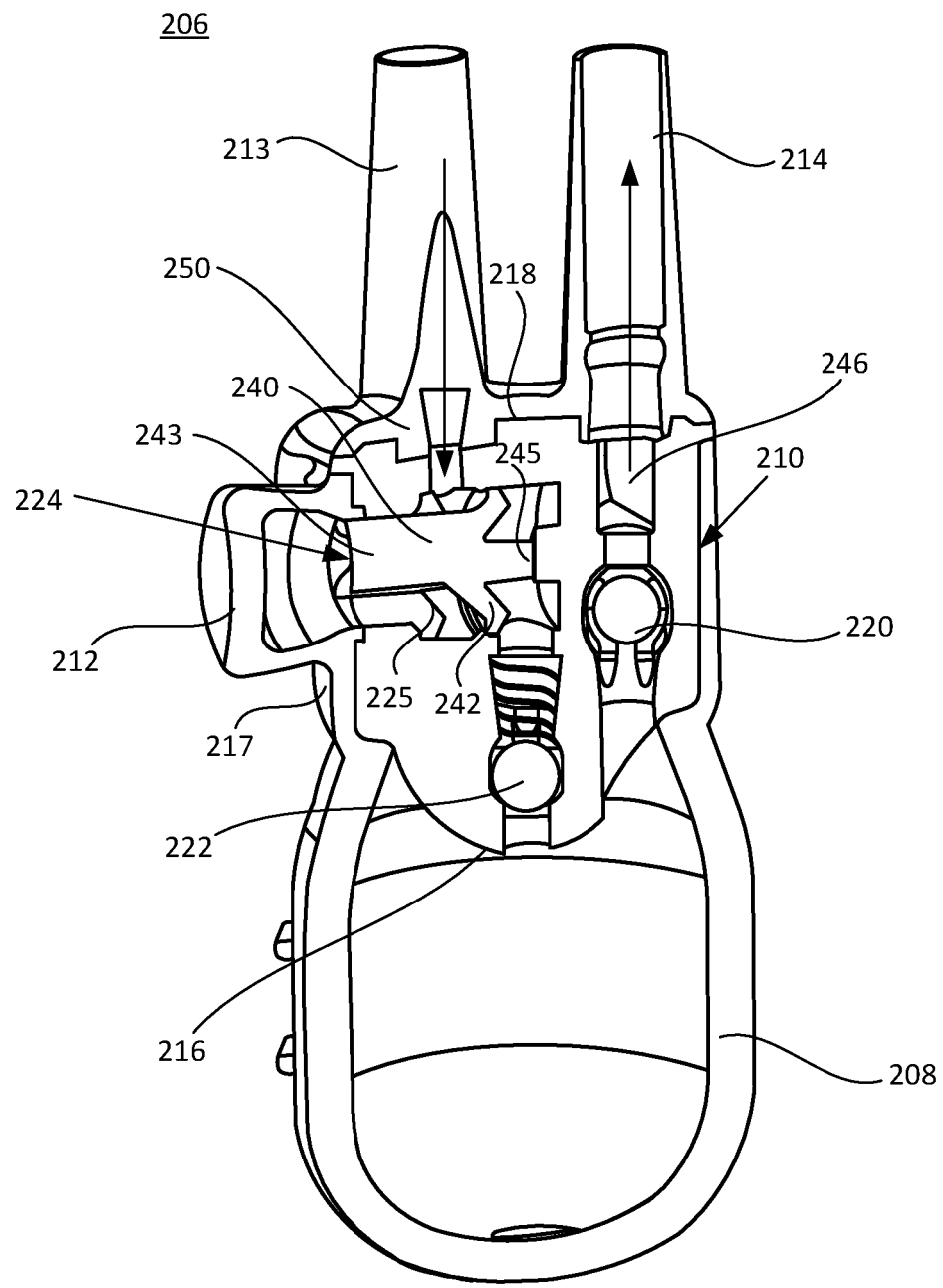
FIG. 2C illustrates a perspective of the pump assembly with the push valve in a deflation position according to an aspect.
Figure 2D:
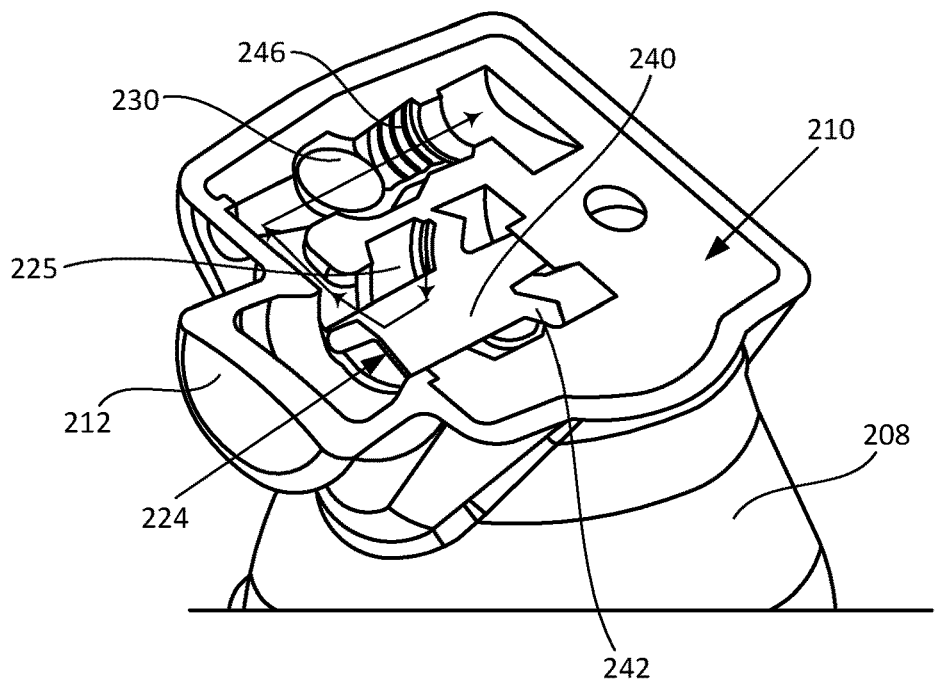
FIG. 2D illustrates a cross-section of a valve body of the pump assembly with the push valve in the deflation position according to an aspect.
Figure 2E:
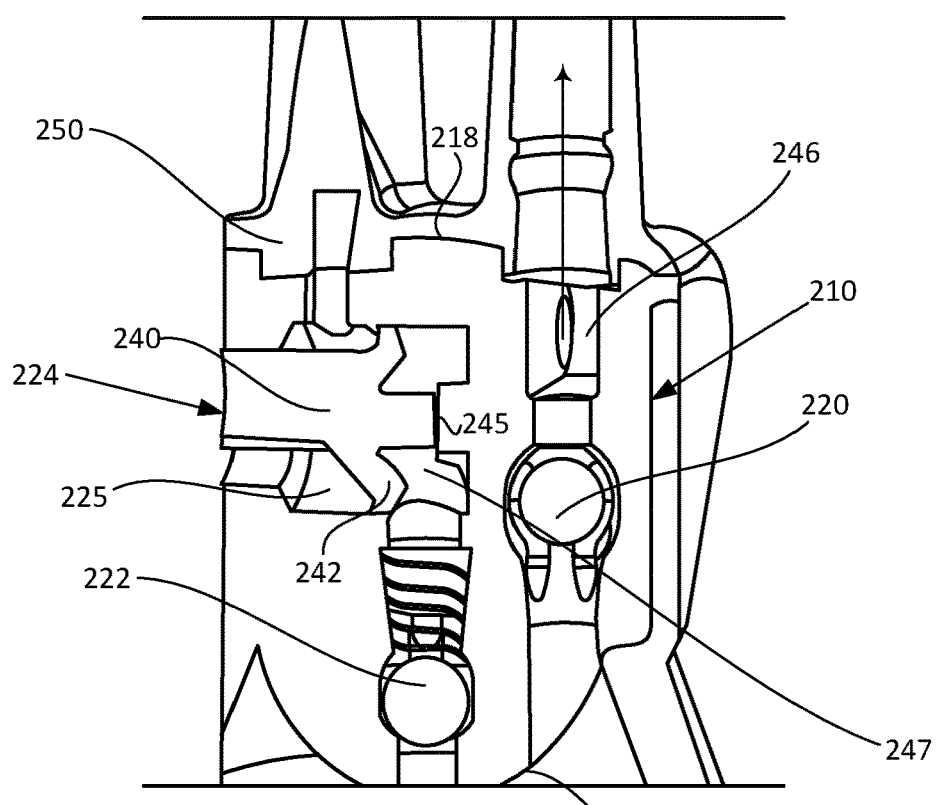
FIG. 2E illustrates a view of the valve body of the pump assembly with the push valve in the deflation position according to an aspect.

FIG. 2A illustrates an exterior of the pump assembly 206 according to an aspect. FIG. 2B illustrates a perspective of the pump assembly 206 with the push valve 224 in an inflation position according to an aspect. FIG. 2C illustrates a perspective of the pump assembly 206 with the push valve 224 in a deflation position according to an aspect. FIG. 2D illustrates a cross-section of a valve body 210 of the pump assembly 206 with the push valve 224 in the deflation position according to an aspect. FIG. 2E illustrates a view of the valve body 210 of the pump assembly 206 with the push valve 224 in the deflation position according to an aspect.

The pump assembly 206 includes a pump bulb 208, the valve body 210, the push valve 224, a button component 212, and fluid transfer ports such as a first cylinder fluid port 213, a second cylinder fluid port 215, and a fluid reservoir port 214. The fluid reservoir port 214 is configured to be connected to the first conduit connector 103 of FIG. 1, and the first cylinder fluid port 213 and the second cylinder fluid port 215 are configured to be connected to the second conduit connector 105 of FIG. 1. The first cylinder fluid port 213 includes a first tubular member defining a cavity. The second cylinder fluid port 215 includes a second tubular member defining a cavity. The fluid reservoir port 214 includes a third tubular member defining a cavity. In some examples, the first tubular member, the second tubular member, and the third tubular member are disposed parallel to each other.

In some examples, the pump assembly 206 includes a tube adaptor 250. In some examples, the tube adaptor 250 is a triple tube adaptor. The tube adaptor 250 may be a unitary body (e.g., a single piece of material) that defines the first cylinder fluid port 213, the second cylinder fluid port 215, and the fluid reservoir port 214. For example, the tube adaptor 250 may be manufactured separately from the valve body 210, but coupled together during the assembly of the pump assembly 206. The tube adaptor 250 is coupled to the valve body 210. In some examples, the tube adaptor 250 is coupled to the valve body 210 using an interference fit. In some examples, the tube adaptor 250 is coupled to the valve body 210 using an adhesive material and/or one or more fasteners.

The pump bulb 208 may extend from a first end portion 216 of the valve body 210, and the fluid transfer ports may extend from a second end portion 218 of the valve body 210. The valve body 210 includes a side surface 217 that extends on one side of the valve body 210 between the first end portion 216 and the second end portion 218. The button component 212 may extend from the side surface 217 and cover the push valve 224. A user may press the button component 212 to move the push valve 224 to the deflation position. In some examples, a single instantaneous push of the push valve 224 causes the push valve 224 to move to the deflation position (and stay in the deflation position). For example, the user may not need to hold the push valve 224 for a predetermined period of time in order to move the push valve 224 to the deflation position.

The valve body 210 includes passageways and valve components. The valve body 210 may include a silicone material. For example, the valve body 210 may be molded from a silicone material having a medium durometer value. The valve body 210 includes the push valve 224, a refill valve 220, an inflation valve 222, and an anti-auto inflate valve 230. The anti-auto inflate valve 230 is shown with respect to FIG. 2D.

The push valve 224 includes a movable valve element 240 and a biasing member 244 that biases the movable valve element 240 to the inflation position (as shown in FIG. 2B). The button component 212 may be a flexible button-shaped material that extends over the movable valve element 240. In some examples, the button component 212 may be considered a portion of the valve body's housing extends from the side surface 217 of the valve body 210. The biasing member 244 is biased to its elongated length, and, upon depression of movable valve element 240, the biasing member 244 compresses to a shorter length (or compressed state). In some examples, the biasing member 244 includes a spring. In some examples, the movable valve element 240 includes an elongated cylindrical valve member. In some examples, the movable valve element 240 includes a poppet. In some examples, the movable valve element 240 includes a directional control valve. The movable valve element 240 includes a first end portion 243, a ring member 242, and a second end portion 245. The ring member 242 may be a circular portion that extends around a portion of the shaft of the movable valve element 240. In some examples, the ring member 242 includes an annular ring. In some examples, the ring member 242 includes a retainer ring. The ring member 242 is disposed on the movable valve element 240 at a location between the first end portion 243 and the second end portion 245. In some examples, the first end portion 243 includes a ring member. In some examples, the second end portion 245 includes a ring member. In some examples, the second end portion 245 has a size (e.g., diameter) smaller than a size (e.g., diameter) of the first end portion 243. In some examples, the first end portion 245 has a length (e.g., extending along an axis 221) longer than a length (e.g., extending along the axis 221) of the second end portion 245. In some examples, the push valve 224 (or the valve body 210 in general) includes a directional control valve.

The movable valve element 240 (or a portion thereof) is movable within a main bore 225 defined by the valve body 210. For example, in the inflation position, the first end portion 243 of the movable valve element 240 extends from the side surface 217 (but is covered by the button component 212). In some examples, the main bore 225 is a cylindrical cavity. The user may press the movable valve element 240 in the main bore 225 along the axis 221 to the deflation position (as shown in FIGS. 2C through 2E). In some examples, the button component 212 then flexes back to its original shape while the movable valve element 240 remains in the deflation position. In the deflation position, the edge of the second end portion 245 of the movable valve element 240 may be disposed adjacent to (or contact) a protrusion extending from the end of the main bore 225 with the biasing member 244 being compressed. In some examples, in the deflation position, the first end portion 243 of the movable valve element 240 is disposed within the valve body 210 (or substantially aligned with the side surface 217 of the valve body 210).

The pressure in the inflatable member may hold the movable valve element 240 in the deflation position (e.g. cylinder pressure seats the push valve 224). In some examples, the main bore 225 may include one or more protrusions that contact the ring member 242 (and/or another portion of the movable valve element 240) to hold the movable valve element 240 in the deflation position (e.g., preventing the biasing member 244 from pushing the movable valve element 240 to the inflation position). In order to switch to the inflation mode, the user may squeeze the pump bulb 208 and the resulting pressure causes the movable valve element 240 to move back to the inflation position. For example, as shown in FIG. 2E, the portion of the main bore 225 disposed between the ring member 242 and the end of the main bore 225 defines an activation force pressure area 247. When the user squeezes the pump bulb 208, pressure inside of the activation force pressure area 247 increases, which forces the movable valve element 240 to switch to the inflation position.

The anti-auto inflate valve 230 is disposed within a post area 246 of the valve body 210. The post area 246 may be considered a refill and anti-auto inflate post area. For example, the post area 246 is a fluid passageway area that transfers fluid from the fluid reservoir port 214 to refill the pump bulb 208 (in the inflation mode) and also transfers fluid to the fluid reservoir port 214 (in the deflation mode). In some examples, the anti-auto inflate valve 230 includes a check ball. In some examples, the anti-auto inflate valve 230 includes a check ball and a biasing member (e.g., a spring).

The refill valve 220 is disposed in a fluid passageway within the valve body 210 between the fluid reservoir port 214 and the pump bulb 208. The refill valve 220 is used to transfer fluid in the inflation mode, but not used to transfer fluid in the deflation mode. In some examples, the refill valve 220 is a one-way valve. The refill valve 220 may include a floating check ball. In some examples, the refill valve 220 includes a floating check ball with fluting to increase and/or maximize fluid velocity across valve. In some examples, the refill valve 220 is aligned with the fluid reservoir port 214. As shown in FIG. 2B, the fluid reservoir port 214 defines a longitudinal axis 219 and the refill valve 220 is aligned along the longitudinal axis 219. For example, in the inflation mode, fluid flows through the refill valve 220 to the pump bulb 208, and the refill valve 220 is positioned along an axis that is aligned with the longitudinal axis 219 of the fluid reservoir port 214. The refill valve 220 being in-line with the fluid reservoir port 214 may minimize fluid pathway tortuosity, and may decrease the pressure drop across the refill valve 220 to increase refill time. In some examples, the refill valve 220 and the anti-auto inflate valve 230 are disposed within the same fluid passageway within the valve body 210. In some examples, the refill valve 220 is aligned with the anti-auto inflate valve 230. For example, a longitudinal axis of the refill valve 220 may be substantially aligned with a longitudinal axis of the anti-auto inflate valve 230.

The inflation valve 222 is disposed within a fluid passageway within the valve body 210 between the main bore 225 and the pump bulb 208. The inflation valve 222 is used to transfer fluid during the inflation mode, but not used to transfer fluid in the deflation mode. In some examples, the inflation valve 222 is a one-way valve. In some examples, the inflation valve 222 includes a check ball and a biasing member that biases the inflation valve 222 to a sealing position. In some examples, the biasing member of the inflation valve 222 is a spring. In some examples, the size of the check ball of the inflation valve 222 is smaller than the size of the check ball of the refill valve 220. In some examples, the smaller check ball and relatively light spring of the inflation valve 222 may decrease the squeeze force required to overcome the spring load.

In the inflation position (as shown in FIG. 2B), the pump bulb 208 is used to transfer fluid from the fluid reservoir to the inflatable member. For example, the user may depress (or squeeze) the pump bulb 208 and then release the pump bulb 208, and then repeat these operations until the desired rigidity is achieved in the inflatable member. The release of the pump bulb 208 creates a suction force that pulls fluid from the fluid reservoir to the pump bulb 208 as shown by the arrow in FIG. 2B. For example, the fluid flows through the fluid reservoir port 214 and through the valve body 210 and into the pump bulb 208. In the valve body 210, the fluid flows through a fluid passageway that includes the post area 246 and the refill valve 220. The refill valve 220 being in-line with the fluid reservoir port 214 may minimize fluid pathway tortuosity, and may decrease the pressure drop across the refill valve 220 to increase refill time. The fluid does not enter the main bore 225 when being transferred through the fluid passageway from the fluid reservoir port 214 to the pump bulb 208.

The depression (or squeezing) of the pump bulb 208 expels the fluid from the pump bulb 208 to the inflatable member. For example, in the valve body 210, the fluid flows through the inflation valve 222, into the main bore 225 (with the movable valve element 240 in the inflation position), and then out of the main bore 225 into the first and second cylinder fluid ports 213, 215. In the inflation position, the movable valve element 240 blocks a fluid passageway from the main bore 225 to the post area 246 (e.g., preventing fluid from flowing from the main bore 225 to the post area 246 during the inflation mode). Rather, the fluid flows through the main bore 225 between the ring member 242 and the end of the cavity of the main bore 225, and into the first and second cylinder fluid ports 213, 215. In some examples, the fluid pathway from the pump bulb 208 to the first and second cylinder fluid ports 213, 215 may decrease the pressure drop across the inflation valve 222 to allow for faster inflate time and may provide less fluid resistance (thereby requiring less pump bulb squeeze force).

The user may press the movable valve element 240 to move along the axis 221 to the deflation position (as shown in FIGS. 2C, 2D, and 2E). In some examples, the axis 221 is substantially orthogonal (e.g., perpendicular) to the axis 219. In some examples, a single instantaneous push of the movable valve element 240 causes the movable valve element 240 to move to the deflation position (and stay in the deflation position). In the deflation position, the edge of the second end portion 245 of the movable valve element 240 may be disposed adjacent to (or contact) a protrusion at the end of the main bore 225 with the biasing member 244 being in a compressed state. In some examples, due to the pressure inside of the inflatable member, some of the fluid may be automatically transferred from the inflation member to the fluid reservoir via the pump assembly 206 (bypassing the pump bulb 208), and then the user may squeeze the inflatable member to transfer some of the remaining fluid in the inflatable member.

Movement of the movable valve element 240 to the deflation position causes a fluid passageway to open between the main bore 225 and the post area 246 (as shown in FIG. 2D), and closes a fluid passageway from the main bore 225 to the inflation valve 222. The fluid may flow from the first and second cylinder ports 213, 215 into the main bore 225 (via a fluid passageway between the cylinder fluid ports 213, 215 and the main bore 225), and the movable valve element 240 causes the fluid to flow into the post area 246. The fluid flows through the anti-auto inflate valve 230 and into the fluid reservoir port 214 (via a fluid passageway between the post area 246 and the fluid reservoir port 214). In the deflation mode, the fluid is not routed through the pump bulb 208. Also, in the deflation mode, the refill valve 220 and the inflation valve 222 are not used.

FIGS. 3A through 3E illustrate various perspectives of a pump assembly 306 having a push valve 324 configured to move from an inflation position to a deflation position to open a fluid passageway that transfers fluid from an inflatable member to a fluid reservoir in a manner that bypasses a pump bulb 308. In the inflation position, the pump assembly 306 transfers fluid from the fluid reservoir to the inflatable member via the pump bulb 308. However, in the deflation position, the pump assembly 306 transfers fluid from the inflatable member to the fluid reservoir that bypasses the pump bulb 308. In some examples, the push valve 324 is a push rod valve. In some examples, the pump assembly 306 is an example of the pump assembly 106 of FIG. 1, and may include any of the features discussed with reference to the inflatable penile prosthesis 100 of FIG. 1 and/or the pump assembly 206 of FIGS. 2A through 2E. Also, the pump assembly 106 of FIG. 1 and/or the pump assembly 206 of FIGS. 2A through 2E may include any of the features with respect to the pump assembly 306 of FIGS. 3A though 3E.

Figure 3A:
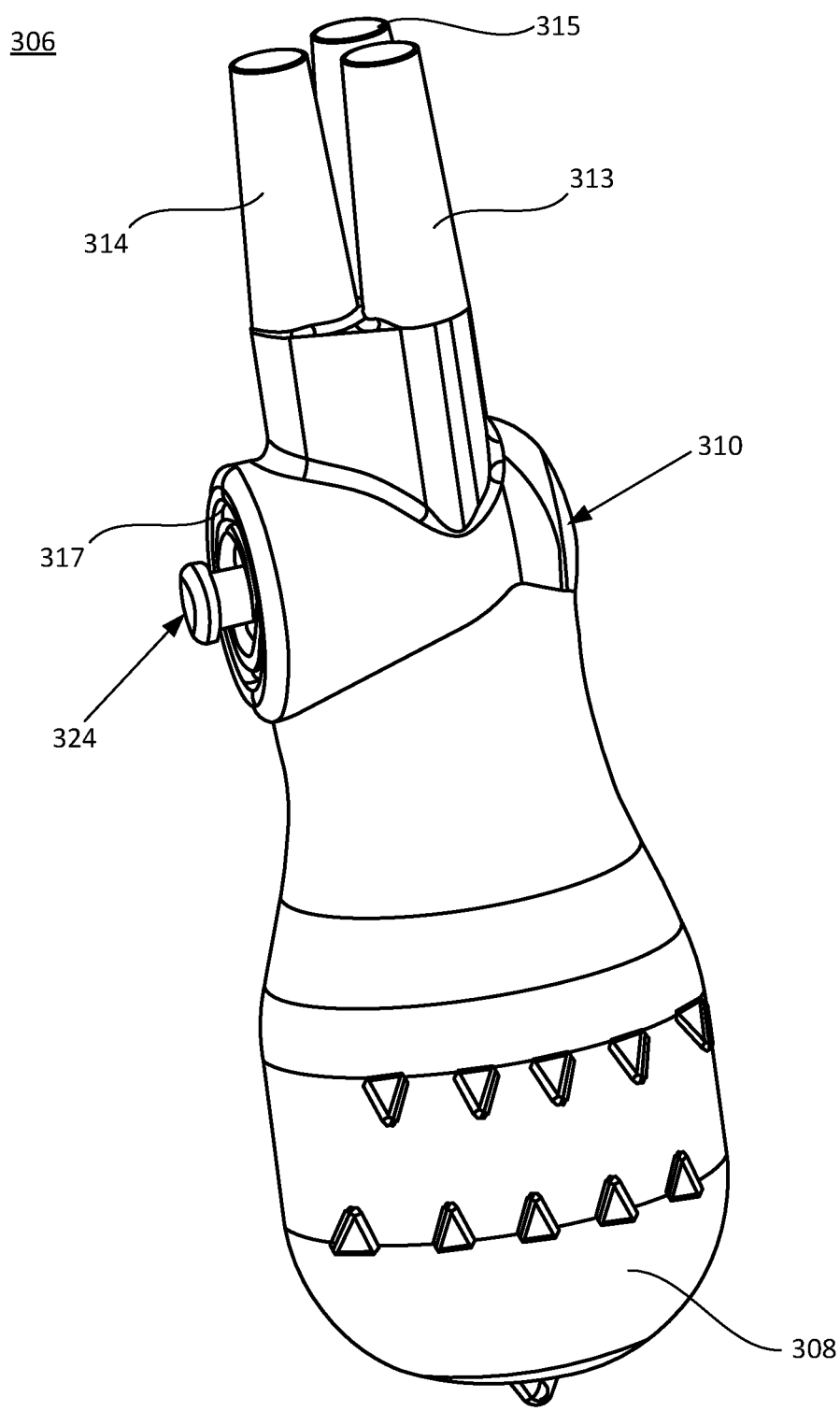
FIG. 3A illustrates a perspective of an exterior of the pump assembly according to an aspect.
Figure 3B:
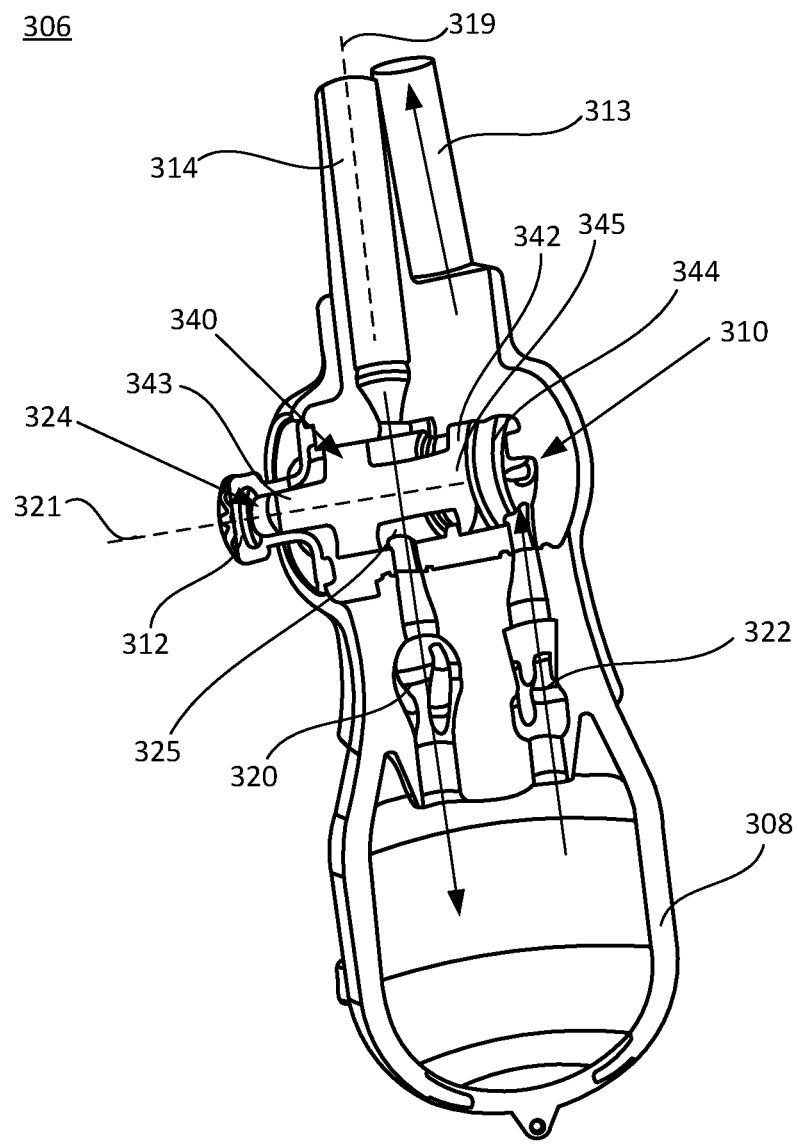
FIG. 3B illustrates a perspective of the pump assembly with the push valve in the inflation position according to an aspect.
Figure 3C:
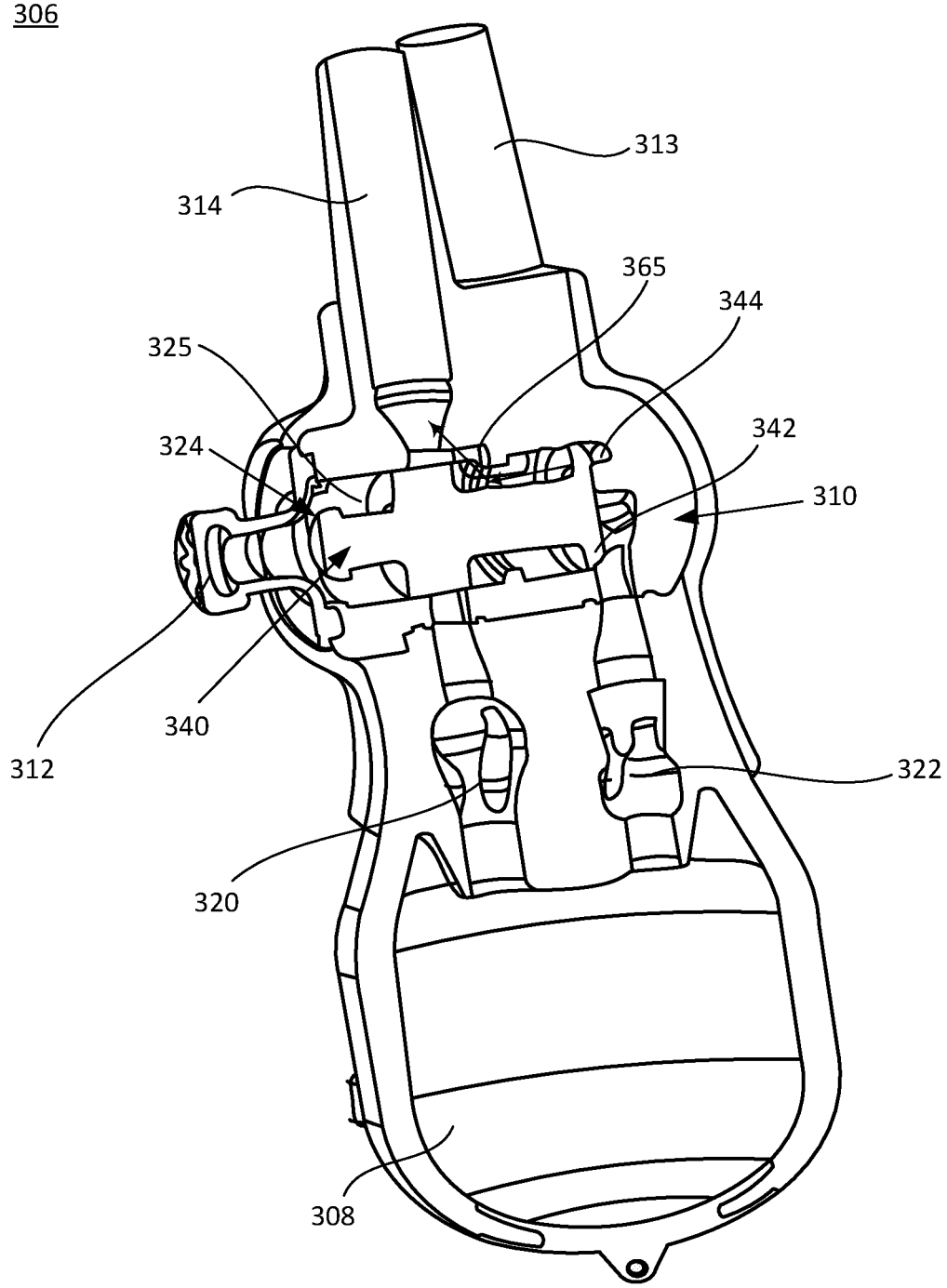
FIG. 3C illustrates a perspective of the pump assembly with the push valve in the deflation position according to an aspect.
Figure 3D:
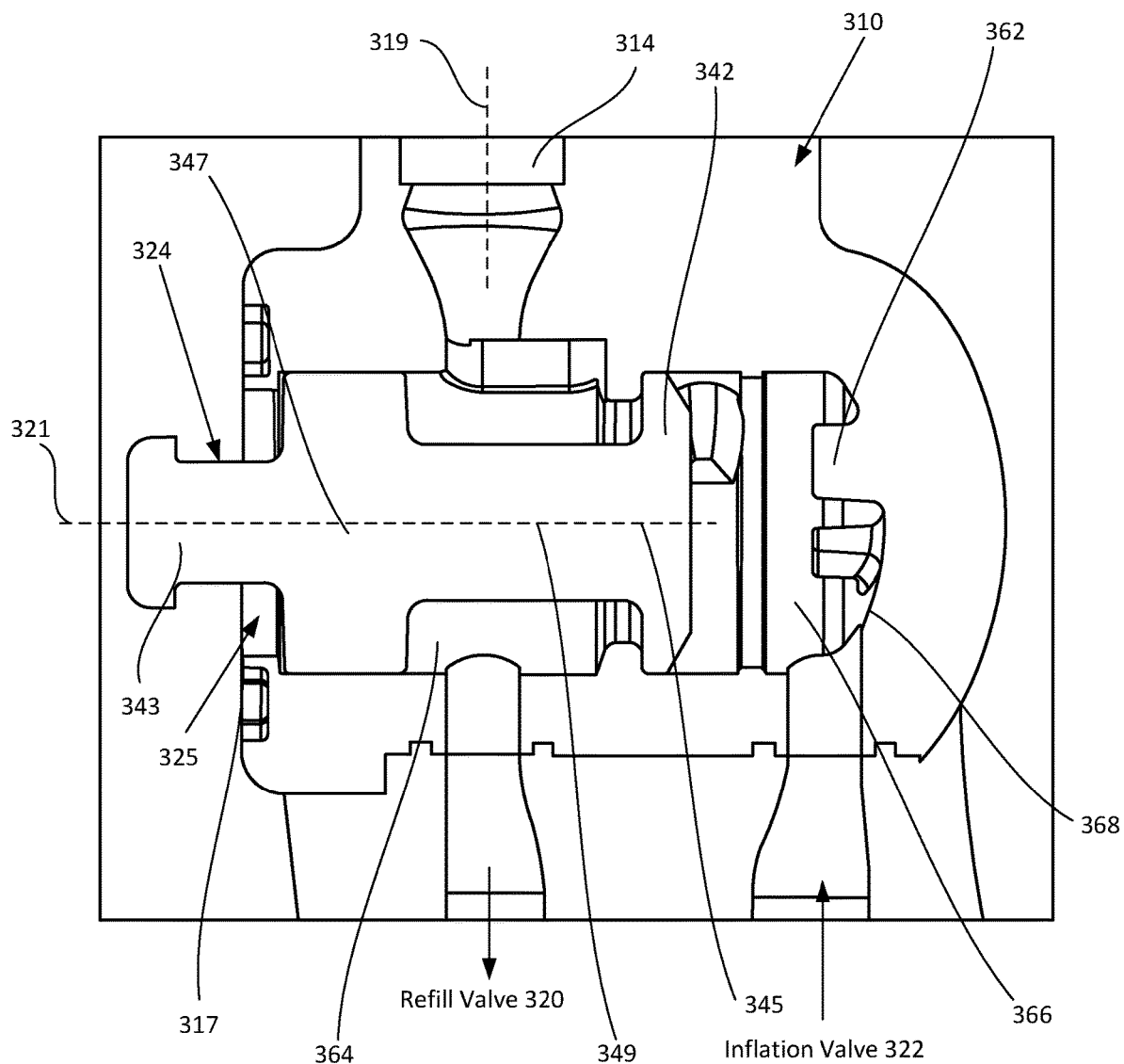
FIG. 3D illustrates a perspective of a valve body of the pump assembly with the push valve in the inflation position according to an aspect.
Figure 3E:
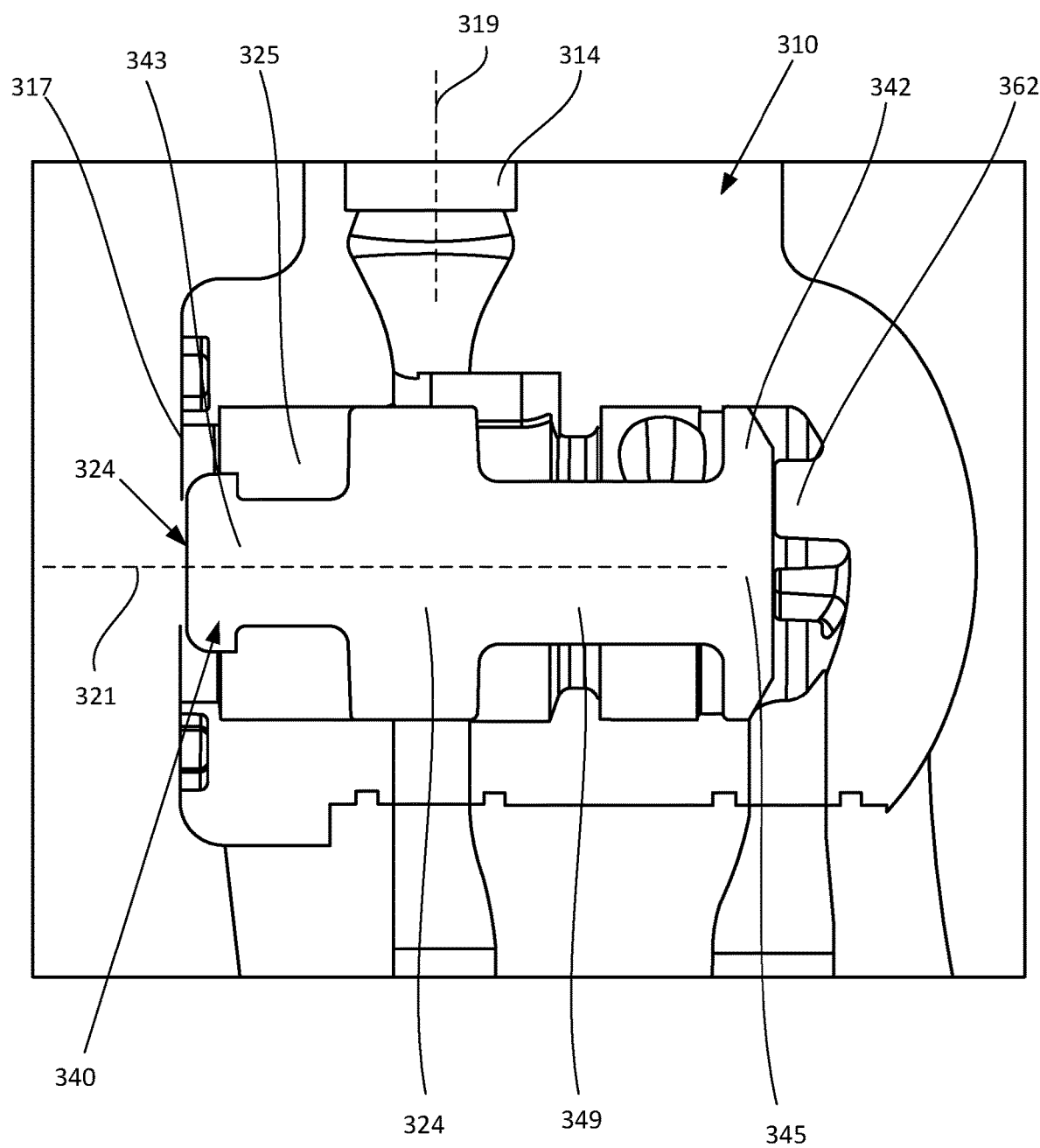
FIG. 3E illustrates a perspective of the valve body with the push valve in the deflation position according to an aspect.

FIG. 3A illustrates a perspective of an exterior of the pump assembly 306 according to an aspect. FIG. 3B illustrates a perspective of the pump assembly 306 with the push valve 324 in the inflation position according to an aspect. FIG. 3C illustrates a perspective of the pump assembly 306 with the push valve 324 in the deflation position according to an aspect. FIG. 3D illustrates a perspective of a valve body 310 of the pump assembly 306 with the push valve 324 in the inflation position according to an aspect. FIG. 3E illustrates a perspective of the valve body 310 with the push valve 324 in the deflation position according to an aspect.

The pump assembly 306 includes the pump bulb 308, the valve body 310, the push valve 324, a button component 312, and fluid transfer ports such as a first cylinder fluid port 313, a second cylinder fluid port 315, and a fluid reservoir port 314. The valve body 310 includes passageways and valve components. The valve body 310 and/or the pump assembly 306 include the push valve 324, a refill valve 320, and an inflation valve 322. In some examples, the valve body 310 includes an anti-auto inflate area 365 (see FIG. 3C) that includes an anti-auto inflate valve. In some examples, the anti-auto inflate valve includes a check ball. In some examples, the anti-auto inflate valve includes a check ball and a biasing member (e.g., a spring).

The push valve 324 includes a movable valve element 340 and a biasing member 344 that biases the movable valve element 340 to the inflation position (as shown in FIG. 3B). As shown in FIGS. 3A and 3B, the button component 312 may be a flexible button-shaped material that extends over the movable valve element 340. In some examples, the button component 312 may be considered a portion of the valve body's housing extends from a side surface 317 of the valve body 310. In some examples, the biasing member 344 includes an elastomer control valve spring. In some examples, the biasing member 344 includes a spring. In some examples, the movable valve element 340 includes an elongated cylindrical valve member. In some examples, the movable valve element 340 is a push rod having sections of different sizes. In some examples, the movable valve element 340 includes a poppet. In some examples, the movable valve element 340 includes a directional control valve.

As shown in greater detail in FIGS. 3D and 3E, the movable valve element 340 includes a first end portion 343, a first central portion 347, a second central portion 349, and a second end portion 345. In some examples, the first end portion 343 includes a button-shaped end that is slightly smaller than the button component 312 such that the first end portion 343 can fit into the button component 312. The second end portion 345 defines a ring member 342. The ring member 342 may be a circular portion that extends around the end of the movable valve element 340. In some examples, the ring member 342 includes an annular ring. In some examples, the ring member 342 includes a retainer ring. The second central portion 349 has a size (e.g., diameter) that is less than a size (e.g., diameter) of the first central portion 347. In some examples, the first end portion 343 has a size (e.g., diameter) that is less than the size of the second central portion 349. In some examples, the second central portion 349 has a length (e.g., extending along an axis 321) longer than a length (e.g., extending along the axis 321) of the first central portion 347. In some examples, the push valve 324 (or the valve body 310 in general) includes a single poppet.

The movable valve element 340 (or a portion thereof) is movable within a main bore 325 defined by the valve body 310. For example, in the inflation position, the first end portion 343 of the movable valve element 340 extends from the side surface 317 (but is covered by the button component 312). In some examples, the main bore 325 is a cylindrical cavity. The user may press the movable valve element 340 to move the movable valve element 340 in the main bore 325 along the axis 321 to the deflation position (as shown in FIGS. 3C and 3D). In some examples, the button component 312 then flexes back to its original shape while the movable valve element 340 remains in the deflation position. In the deflation position, the ring member 342 on the second end portion 345 of the movable valve element 340 may be disposed adjacent to the end of the main bore 325 and/or in contact with a portion 362 of the valve body 310 that slightly extends into the main bore 325. In the deflation position, the biasing member 344 is compressed. In some examples, in the deflation position, the edge of the first end portion 343 of the movable valve element 340 may be disposed within the valve body 310 and/or substantially aligned with the side surface 317 of the valve body 310.

The pressure in the inflatable member may hold the movable valve element 340 in the deflation position (e.g. cylinder pressure seats the push valve 324). In some examples, the main bore 325 may include one or more protrusions that contact the ring member 342 (and/or another portion of the movable valve element 340) to hold the movable valve element 340 in the deflation position. In some examples, the biasing member 344 is configured to return the movable valve element 340 to the inflation position in response to the cylinder pressure dropping below a threshold level. In some examples, the user may squeeze the pump bulb 308 and the resulting pressure causes the movable valve element 340 to move back to the inflation position.

The refill valve 320 is disposed in a fluid passageway between the main bore 325 and the pump bulb 308. The refill valve 320 is used to transfer fluid in the inflation mode, but not used to transfer fluid in the deflation mode. In some examples, the refill valve 320 is a one-way valve. The refill valve 320 may include a floating check ball. In some examples, the refill valve 320 includes a floating check ball with fluting to increase and/or maximize fluid velocity across valve. In some examples, the refill valve 320 is aligned with the fluid reservoir port 314. The fluid reservoir port 314 defines a longitudinal axis 319 and the refill valve 320 is aligned along the longitudinal axis 319. For example, in the inflation mode, fluid flows through the refill valve 320 to the pump bulb 308, and the refill valve 320 is positioned along an axis that is aligned with the longitudinal axis 319 of the fluid reservoir port 314. The refill valve 320 being in-line with the fluid reservoir port 314 may minimize fluid pathway tortuosity, and may decrease the pressure drop across the refill valve 320 to increase refill time.

The inflation valve 322 is disposed within a fluid passageway between the main bore 325 and the pump bulb 308. In some examples, the inflation valve 322 is disposed in a separate fluid passageway than the refill valve 320. In some examples, the inflation valve 322 and the refill valve 320 are parallel to each other. The inflation valve 322 is used to transfer fluid during the inflation mode, but not used to transfer fluid in the deflation mode. In some examples, the inflation valve 322 is a one-way valve. In some examples, the inflation valve 322 includes a check ball and a biasing member that biases the inflation valve 322 to a sealing position. In some examples, the biasing member of the inflation valve 322 is a spring. In some examples, the size of the check ball of the inflation valve 322 is smaller than the size of the check ball of the refill valve 320. In some examples, the smaller check ball and relatively light spring of the inflation valve 322 may decrease the squeeze force required to overcome the spring load.

In the inflation position (as shown in FIGS. 3B and 3D), the pump bulb 308 is used to transfer fluid from the fluid reservoir to the inflatable member. For example, the user may depress (or squeeze) the pump bulb 308 and then release the pump bulb 308, and then repeat these operations until the desired rigidity is achieved in the inflatable member. The release of the pump bulb 308 creates a suction force that pulls fluid from the fluid reservoir to the pump bulb 308 as shown by the arrow in FIG. 3B. For example, the fluid flows through the fluid reservoir port 314, through the valve body 310, through the refill valve 320, and into the pump bulb 308. In the valve body 310, the fluid flows from the fluid reservoir port 314 into a portion 364 of the main bore 325. In the inflation position, the portion 364 of the main bore 325 is a bore portion between the first central portion 347 of the movable valve element 340 and the ring member 342 of the movable valve element 340. In the inflation position, the second central portion 349 (e.g., having the reduced size) of the movable valve element 340 is positioned in the main bore 325 such that the movable valve element 340 directs the flow of fluid around the second central portion 349 and into the fluid passageway having the refill valve 320.

The depression (or squeezing) of the pump bulb 308 expels the fluid from the pump bulb 308 to the inflatable member. For example, the fluid flows from the pump bulb 308, through the inflation valve 322, into a portion 366 of the main bore 325, and then into the first and second cylinder fluid ports 313, 315. In the inflation position, the portion 366 of the main bore 325 is a bore portion disposed between the ring member 342 of the movable valve element 340 and an end 368 of the main bore 325. For instance, in the inflation position, the ring member 342 may separate the fluid passageway in the main bore 325 from the fluid reservoir port 314 to the pump bulb 308 and the fluid passageway in the main bore 325 from the pump bulb 308 to the first and second cylinder fluid ports 313, 315. In some examples, the fluid pathway from the pump bulb 308 to the first and second cylinder fluid ports 313, 315 may decrease the pressure drop across the inflation valve 322 to allow for faster inflate time and may provide less fluid resistance (thereby requiring less pump bulb squeeze force).

The user may press the movable valve element 340 to move along the axis 321 to the deflation position (as shown in FIGS. 3C and 3E). In some examples, the axis 321 is substantially orthogonal (e.g., perpendicular) to the axis 319. In some examples, a single instantaneous push of the movable valve element 340 causes the movable valve element 340 to move to the deflation position (and stay in the deflation position). In the deflation position, the biasing member 344 is compressed, and the ring member 342 contacts a portion 362 of the valve body 310 that extends into the main bore 325. In some examples, due to the pressure inside of the inflatable member, some of the fluid may be automatically transferred from the inflation member to the fluid reservoir via the pump assembly 306 (bypassing the pump bulb 308), and then the user may squeeze the inflatable member to transfer some of the remaining fluid in the inflatable member.

Movement of the movable valve element 340 to the deflation position closes the fluid passageway in the main bore 325 between the fluid reservoir port 314 and the pump bulb 308 and closes the fluid passageway in the valve body 310 between the pump bulb 308 and the first and second cylinder ports 313, 315. As shown in FIG. 3C, in the deflation position, the fluid may flow through a portion of the main bore 325 between the ring member 342 and the first central portion 347. In the deflation mode, the fluid is not routed through the pump bulb 308. Also, in the deflation mode, the refill valve 320 and the inflation valve 322 are not used.

Figure 4A:
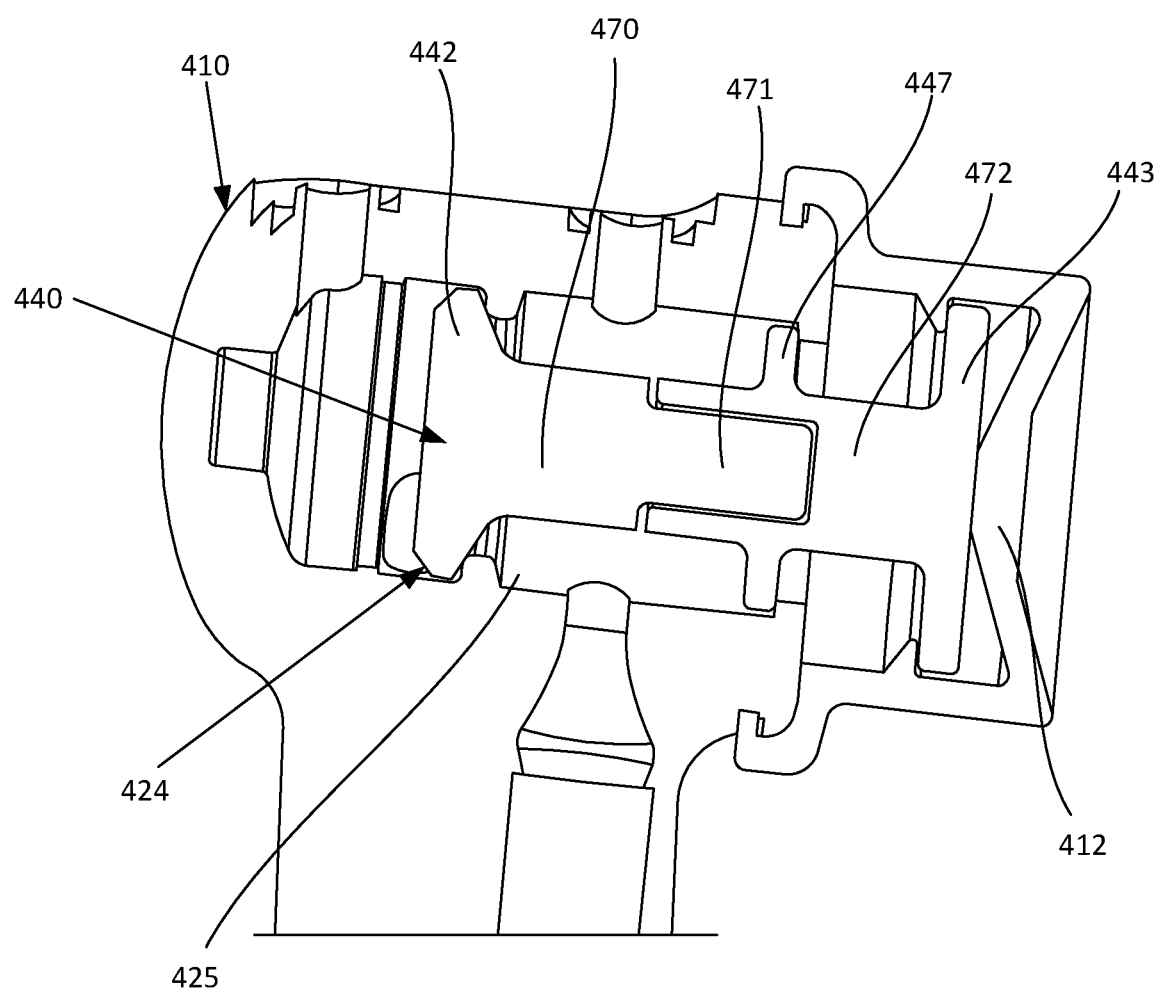
FIG. 4A illustrates a perspective of the push valve according to an aspect.
Figure 4B:
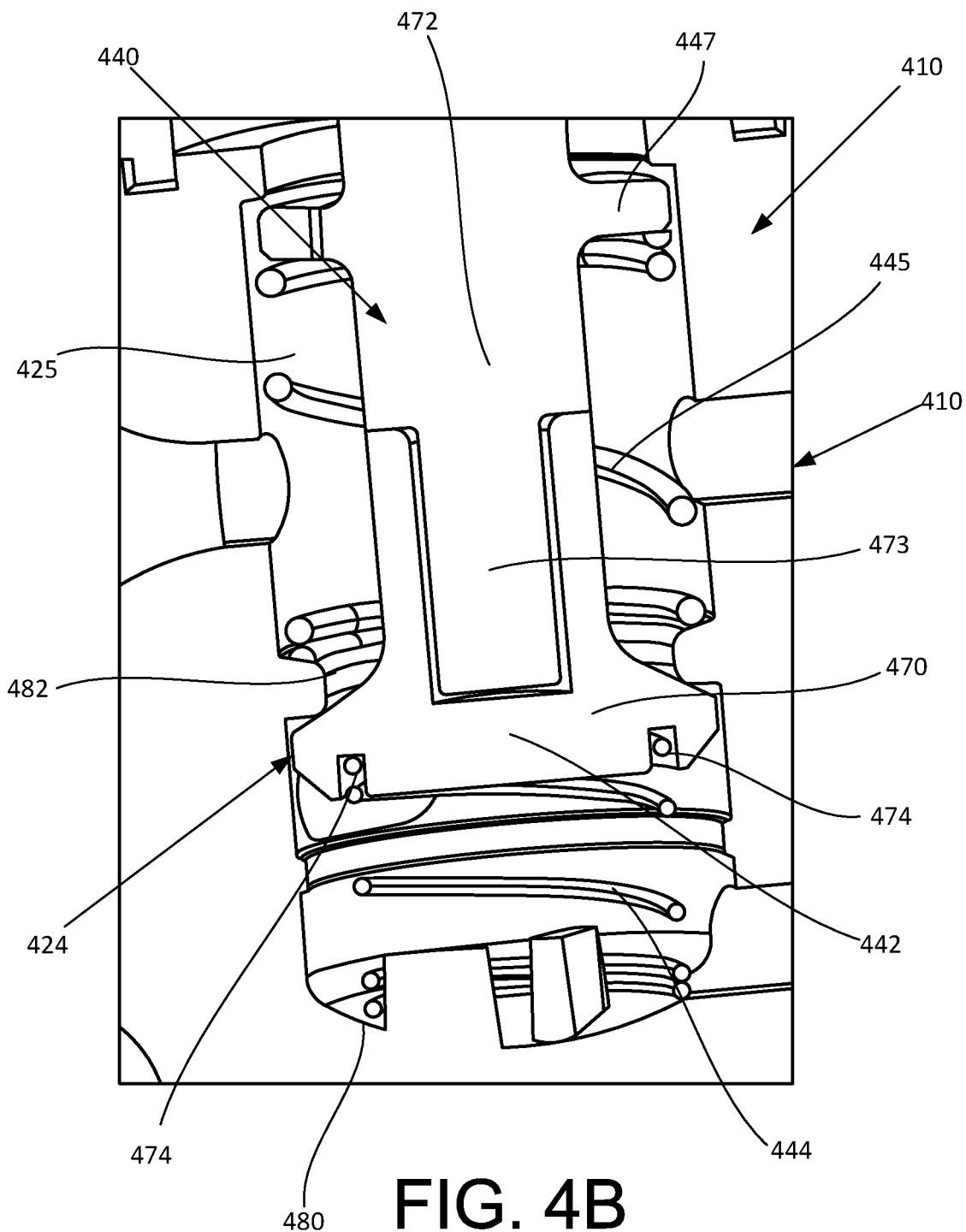
FIG. 4B illustrates a perspective of the push valve in the inflation position according to an aspect.
Figure 4C:
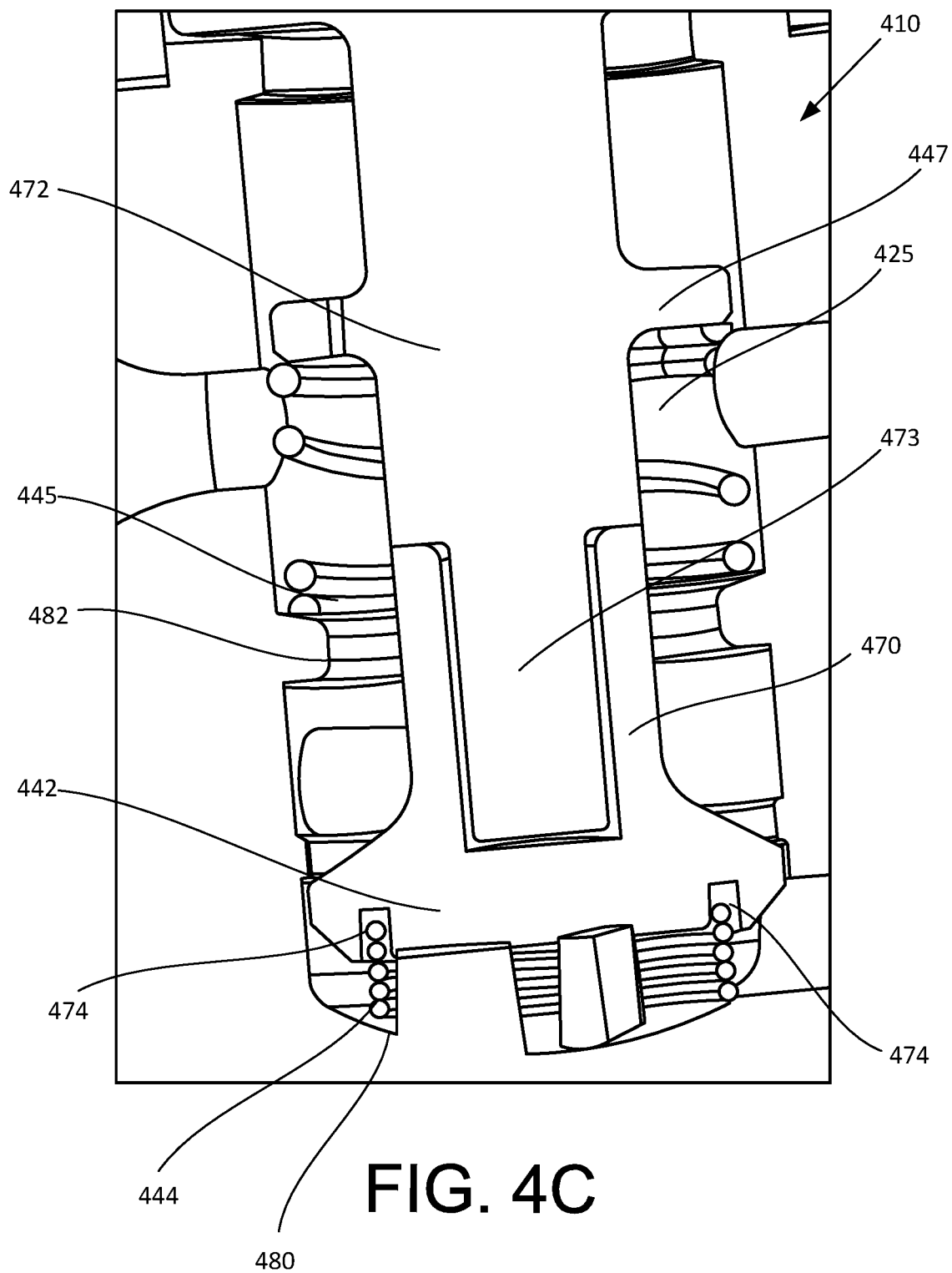
FIG. 4C illustrates a perspective of the push valve in the deflation position according to an aspect.

FIGS. 4A through 4C illustrates a push valve 424 according to an aspect. The push valve 424 may be an example of any of the push valves discussed with reference to the previous figures, and may include any of the features discussed herein. FIG. 4A illustrates a perspective of the push valve 424 according to an aspect. FIG. 4B illustrates a perspective of the push valve 424 in the inflation position according to an aspect. FIG. 4C illustrates a perspective of the push valve 424 in the deflation position according to an aspect.

The push valve 424 includes a two-piece movable valve element 440. The movable valve element 440 includes a first movable member 470 and a second movable member 472. The first movable member 470 and the second movable member 472 are unitary bodies that are separate from each other. The first movable member 470 and the second movable member 472 are concentrically aligned. The first movable member 470 and the second movable member 472 are configured to move independently of each other within a main bore 425 of a valve body 410. The push valve 424 includes a first biasing member 444 that biases the first movable member 470 to the inflation position, and a second biasing member 445 that biases the second movable member 472 to the inflation position. The first biasing member 444 and the second biasing member 445 are configured to be compressed upon an application of force. In some examples, the first biasing member 444 includes a spring having a plurality of coils. In some examples, the second biasing member 445 includes a spring having a plurality of coils.

The first movable member 470 may be a cylindrical body having sections with different sizes (e.g., diameters). The second movable member 472 may be a cylindrical body having sections with different sizes (e.g., diameters). The first movable member 470 includes a ring member 442 disposed on one end portion of the first movable member 470 and an interfacing portion 471 disposed on the other end portion of the first movable member 470. The second movable member 472 includes a ring member 443 disposed on one end portion of the second movable member 472, an interfacing portion 473 disposed on the other end portion of the second movable member 472, and a ring member 447 disposed on the second movable member 472 at a location between the interfacing portion 473 and the ring member 443. The ring members 442, 443, 447 may be circular portions that extend around portions of the first movable member 470 or the second movable member 472. In some examples, the ring members 442, 443, 447 may be annular rings or retainer rings.

The interfacing portion 471 of the first movable member 470 may be movably coupled (e.g., contact and slide) with respect to the interfacing portion 473 of the second movable member 472. In some examples, the interfacing portion 471 may overlap with the interfacing portion 473 and may move away from each other such that the interfacing portion 471 and the interfacing portion 473 partially overlap (or do not overlap at all). In some examples, each of the interfacing portion 471 and the interfacing portion 473 has a width that is narrower than other portions of the first movable member 470 and the second movable member 472, respectively. In some examples, the first movable member 470 defines a channel or groove on a surface portion of the first movable member 470 that is configured to receive the interfacing portion 473 of the second movable member 472, and the second movable member 472 defines a channel or groove on a surface portion of the second movable member 472 that is configured to receive the interfacing portion 471 of the first movable member 470.

A user may press the button component 412 that causes the first movable member 470 and the second movable member 472 to linearly move to the deflation position in which the first biasing member 444 and the second biasing member 445 are compressed. The first biasing member 444 is disposed in the main bore 425, and contacts the ring member 442 on the first movable member 470. For example, the first biasing member 444 may be disposed between the ring member 442 and an end portion 480 of the main bore 425. The ring member 442 defines slots 474 that receive coil portions of the first biasing member 444. For example, the first biasing member 444 contacts the ring member 442 at the slots 474 to bias the first movable member 470 to the inflation position. The second biasing member 445 is disposed in the main bore 425, and contacts the ring member 447 on the second movable member 472. For example, the second biasing member 445 may be disposed between the ring member 447 and a portion 482 of the valve body 410 in the main bore 425. The second biasing member 445 contacts the ring member 447 to bias the second movable member 472 to the inflation position. In some examples, the ring member 447 includes slots that receive coils portions of the second biasing member 445.

FIGS. 5A through 5D illustrate various perspectives of a pump assembly 506 having a push valve 524 configured to move from an inflation position to a deflation position to open a fluid passageway that transfers fluid from an inflatable member to a fluid reservoir in a manner that bypasses a pump bulb 508. In some examples, the push valve 524 is a switching valve pump. The pump assembly 506 may include any of the features discussed with reference to the inflatable penile prosthesis 100 of FIG. 1, the pump assembly 206 of FIGS. 2A through 2E, the pump assembly 306 of FIGS. 3A through 3D, and/or the push valve 424 of FIGS. 4A through 4C. Also, the pump assembly 106 of FIG. 1, the pump assembly 206 of FIGS. 2A through 2E, the pump assembly 306 of FIGS. 3A through 3D, and/or the push valve 424 of FIGS. 4A through 4C may include any of the features with respect to the pump assembly 506 of FIGS. 5A though 3D.

Figure 5A:
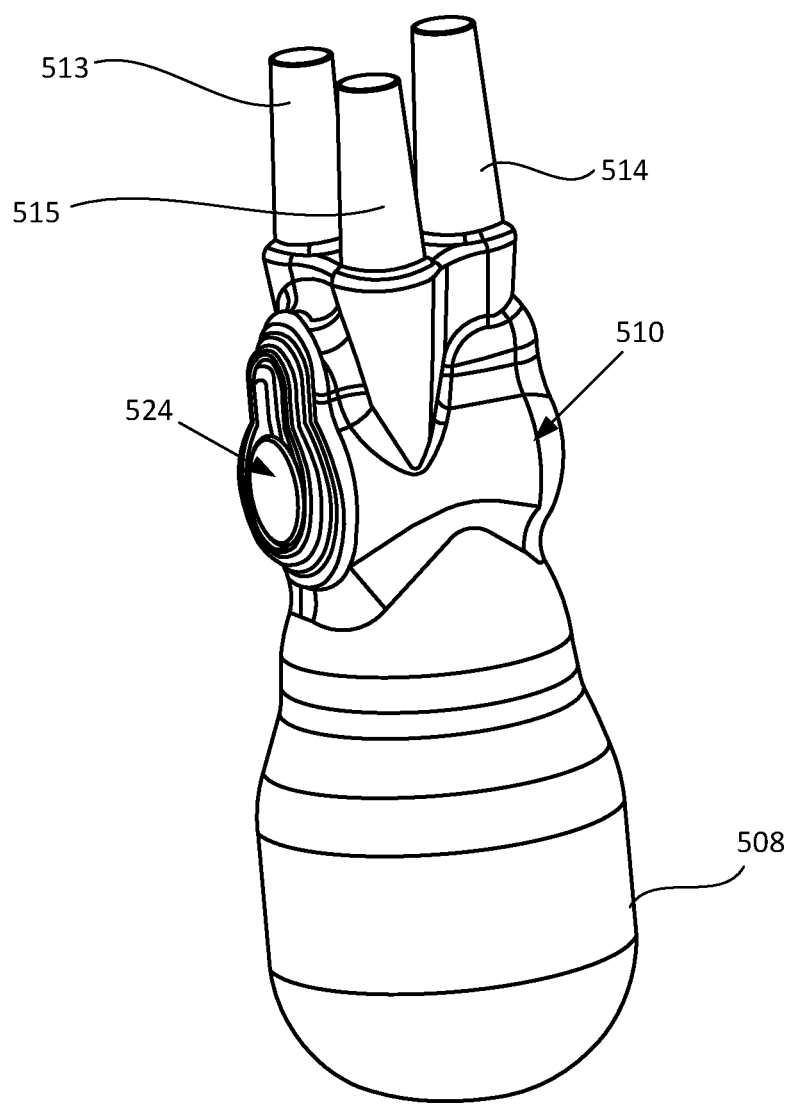
FIG. 5A illustrates a perspective of an exterior of the pump assembly with the push valve in the deflation position according to an aspect.
Figure 5B:
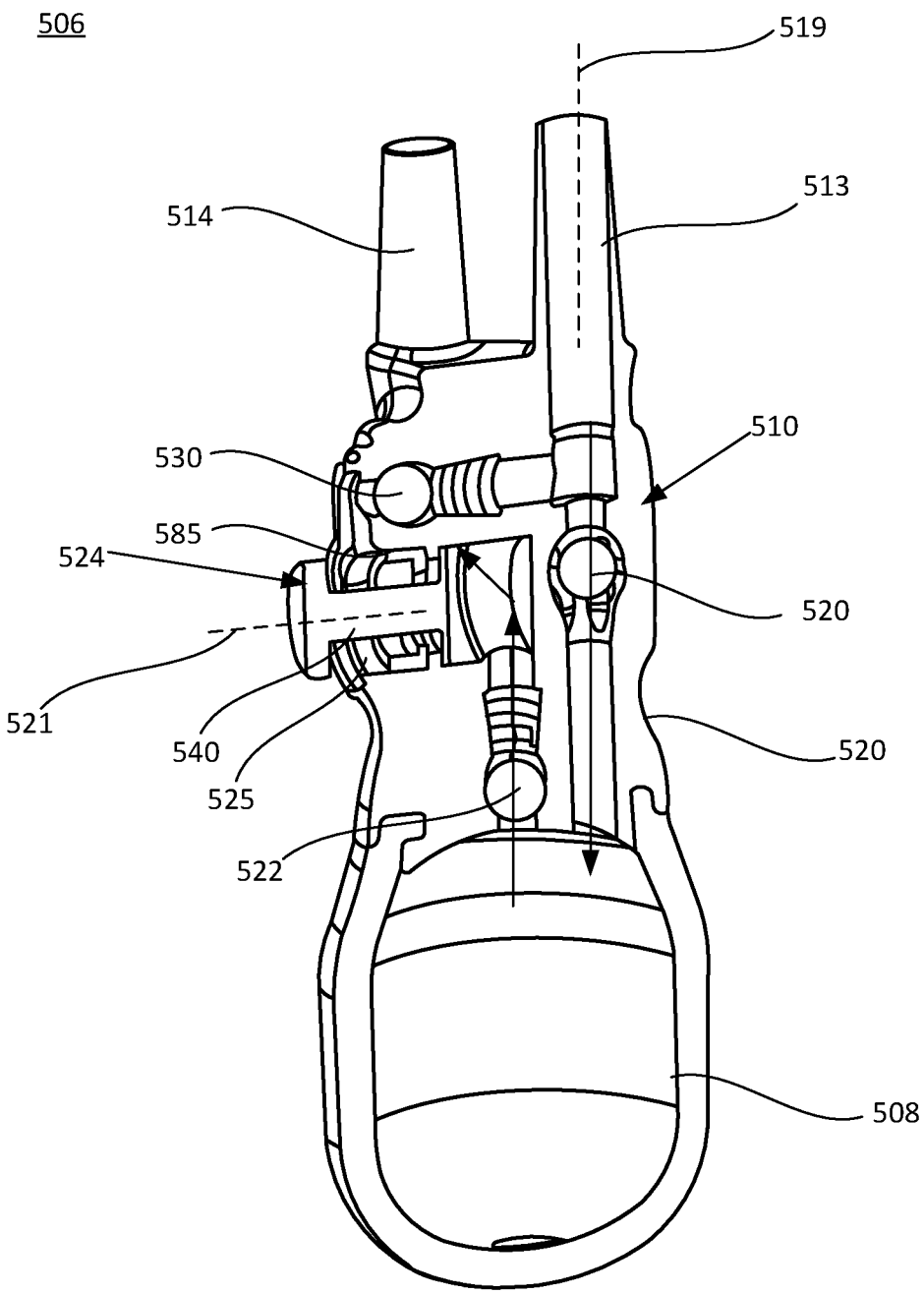
FIG. 5B illustrates a perspective of the pump assembly with the push valve in the inflation position according to an aspect.
Figure 5C:
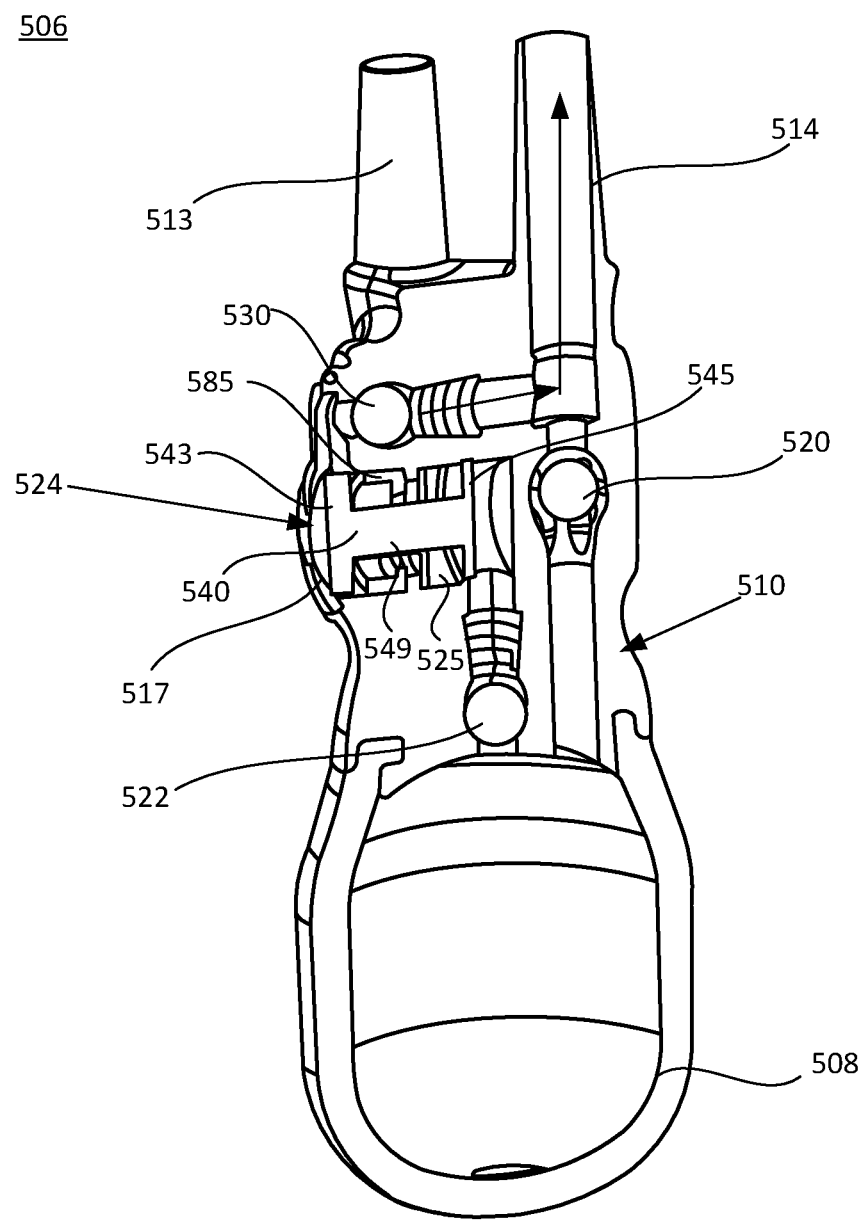
FIG. 5C illustrates a perspective of the pump assembly with the push valve in the deflation position according to an aspect.
Figure 5D:
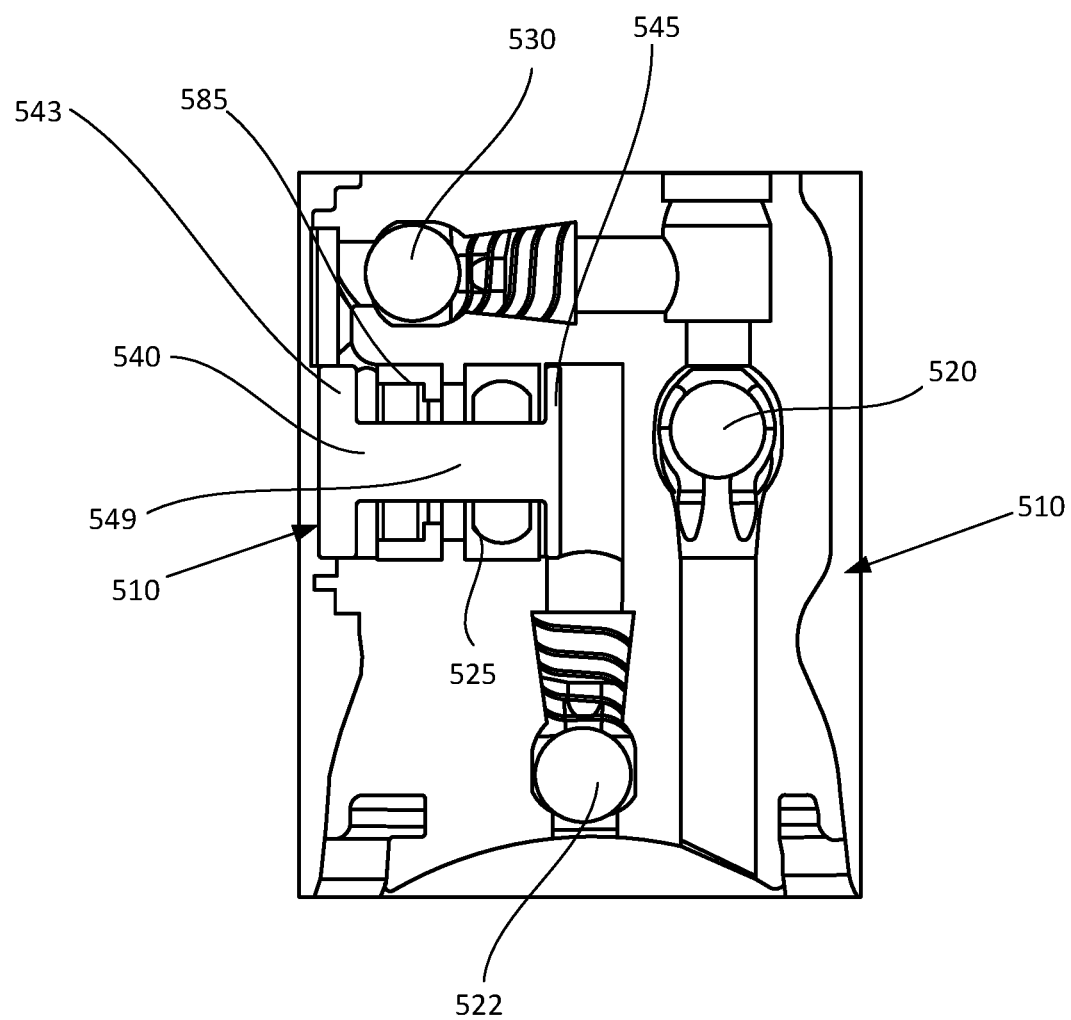
FIG. 5D illustrates a perspective of a valve body of the pump assembly with the push valve in the deflation position according to an aspect.

FIG. 5A illustrates a perspective of an exterior of the pump assembly 506 with the push valve 524 in the deflation position according to an aspect. FIG. 5B illustrates a perspective of the pump assembly 506 with the push valve 524 in the inflation position according to an aspect. FIG. 5C illustrates a perspective of the pump assembly 506 with the push valve 524 in the deflation position according to an aspect. FIG. 5D illustrates a perspective of a valve body 510 of the pump assembly 506 with the push valve 524 in the deflation position according to an aspect.

The pump assembly 506 includes the pump bulb 508, the valve body 510, the push valve 524 movable with respect to the valve body 510, and fluid transfer ports such as a first cylinder fluid port 513, a second cylinder fluid port 515, and a fluid reservoir port 514. In some examples, the pump assembly 506 includes a button component that covers the push valve 524. The valve body 510 includes passageways and valve components. The valve body 510 includes the push valve 524, a refill valve 520, an inflation valve 522, and an anti-auto inflate valve 530.

The push valve 524 includes a movable valve element 540 and a biasing member (not shown) that biases the movable valve element 540 to the inflation position (as shown in FIG. 5B). The push valve 524 may include a valve guide 585. In the inflation position, a portion of the movable valve element 540 extends from a side surface 517 of the valve body 510. In some examples, the biasing member includes a spring. In some examples, the movable valve element 540 includes an elongated cylindrical valve member. In some examples, the movable valve element 540 is a push rod having sections of different sizes. In some examples, the movable valve element 540 includes a poppet. In some examples, the movable valve element 540 includes a directional control valve.

The movable valve element 540 includes a first end portion 543, a central portion 549, and a second end portion 545. In some examples, the central portion 549 has a size (e.g., diameter) less than a size (e.g., diameter) of the first end portion 543 and a size (e.g., diameter) of the second end portion 545. In some examples, the first end portion 543 includes a ring member. In some examples, the second end portion 545 includes a ring member. In some examples, the ring member includes an annular ring or a retainer ring. The central portion 549 has a length longer than a length of the first end portion 543 and longer than a length of the second end portion 545.

In some examples, the pressure in the inflatable member may hold the movable valve element 540 in the deflation position (e.g. cylinder pressure seats the push valve 524). In some examples, the main bore 525 may include one or more protrusions that contact one or more portions of the movable valve element 540 to hold the movable valve element 540 in the deflation position. In some examples, the user may squeeze the pump bulb 508 and the resulting pressure causes the movable valve element 540 to move back to the inflation position.

The refill valve 520 is disposed in a fluid passageway between the fluid reservoir port 514 and the pump bulb 508. The refill operation does not pass through the main bore 525 so there may be less fluid resistance in the refill state. The refill valve 520 is used to transfer fluid in the inflation mode, but not used to transfer fluid in the deflation mode. In some examples, the refill valve 520 is a one-way valve. The refill valve 520 may include a floating check ball. In some examples, the refill valve 520 includes a floating check ball with fluting to increase and/or maximize fluid velocity across valve. In some examples, the refill valve 520 is aligned with the fluid reservoir port 514. The fluid reservoir port 514 defines a longitudinal axis 519 and the refill valve 520 is aligned along the longitudinal axis 519. For example, in the inflation mode, fluid flows through the refill valve 520 to the pump bulb 508, and the refill valve 520 is positioned along an axis that is aligned with the longitudinal axis 519 of the fluid reservoir port 514. The refill valve 520 being in-line with the fluid reservoir port 514 may minimize fluid pathway tortuosity, and may decrease the pressure drop across the refill valve 520 to increase refill time.

The inflation valve 522 is disposed within a fluid passageway between the main bore 525 and the pump bulb 508. In some examples, the inflation valve 522 is disposed in a separate fluid passageway than the refill valve 520. In some examples, the inflation valve 522 and the refill valve 520 are parallel to each other. The inflation valve 522 is used to transfer fluid during the inflation mode, but not used to transfer fluid in the deflation mode. In some examples, the inflation valve 522 is a one-way valve. In some examples, the inflation valve 522 includes a check ball and a biasing member that biases the inflation valve 522 to a sealing position. In some examples, the biasing member of the inflation valve 522 is a spring. In some examples, the size of the check ball of the inflation valve 522 is smaller than the size of the check ball of the refill valve 520. In some examples, the smaller check ball and relatively light spring of the inflation valve 522 may decrease the squeeze force required to overcome the spring load.

In the inflation position, the pump bulb 508 is used to transfer fluid from the fluid reservoir to the inflatable member. For example, the user may depress (or squeeze) the pump bulb 508 and then release the pump bulb 508, and then repeat these operations until the desired rigidity is achieved in the inflatable member. The release of the pump bulb 508 creates a suction force that pulls fluid from the fluid reservoir to the pump bulb 308 as shown by the arrow in FIG. 5B. For example, the fluid flows through the fluid reservoir port 514, the refill valve 520, and into the pump bulb 508.

The depression (or squeezing) of the pump bulb 508 expels the fluid from the pump bulb 508 to the inflatable member. For example, the fluid flows from the pump bulb 508, through the inflation valve 522, into a portion of the main bore 525, and then into the first and second cylinder fluid ports 513, 515. The second end portion 545 of the movable valve element 540 directs the fluid into the first and second cylinder fluid ports 513, 515. In some examples, the fluid pathway from the pump bulb 508 to the first and second cylinder fluid ports 513, 515 may decrease the pressure drop across the inflation valve 522 to allow for faster inflate time and may provide less fluid resistance (thereby requiring less pump bulb squeeze force).

The user may press the movable valve element 540 to move along the axis 521 to the deflation position. In some examples, the axis 521 is substantially orthogonal (e.g., perpendicular) to the axis 519. In some examples, a single instantaneous push of the movable valve element 540 moves the movable valve element 540 to the deflation position (and stay in the deflation position). As shown in FIG. 5C, in the deflation position, the fluid may flow from the first and second cylinder fluid ports 513, 515, through the anti-auto inflate valve 530, and into the fluid reservoir port 514. In the deflation mode, the fluid is not routed through the pump bulb 508. Also, in the deflation mode, the refill valve 520 and the inflation valve 522 are not used.

Figure 6A:
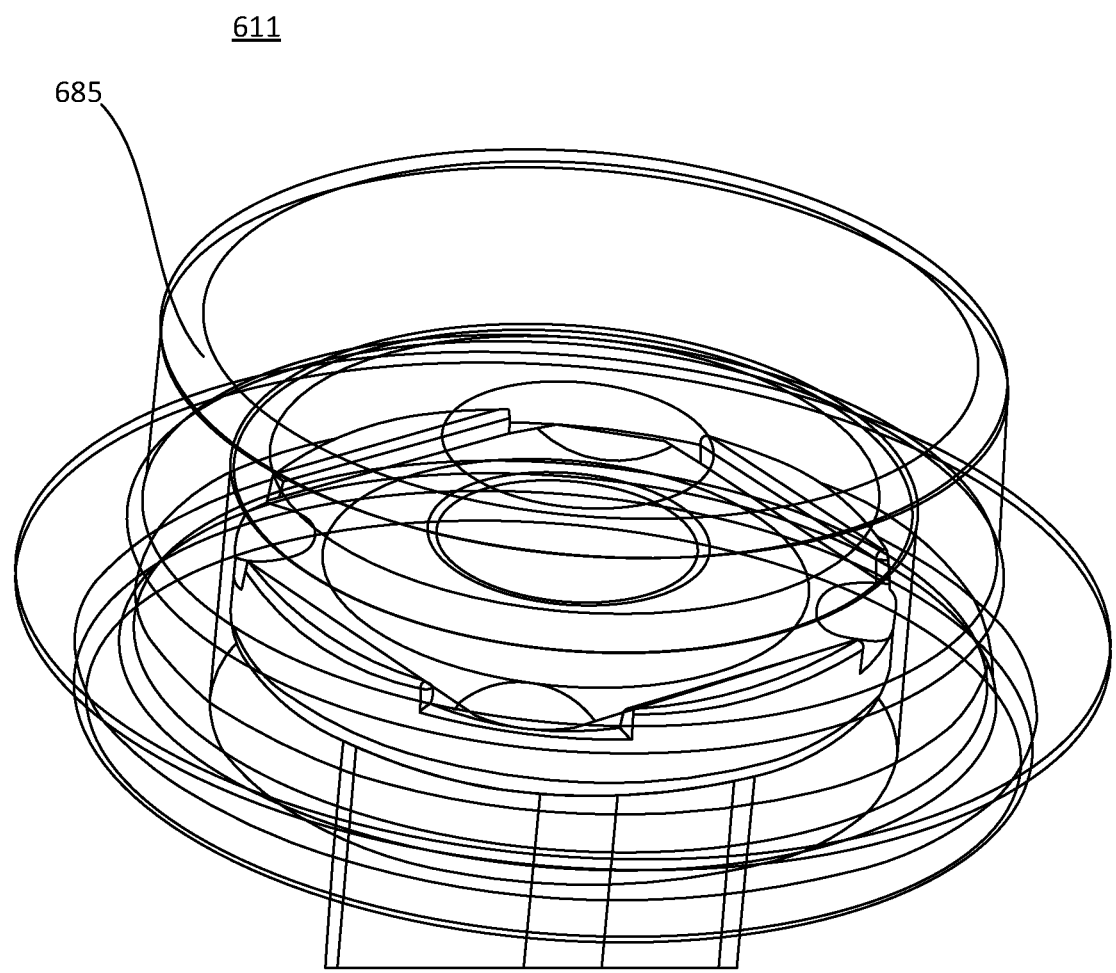
FIG. 6A illustrates a feedback component as a dome structure according to an aspect.
Figure 6B:
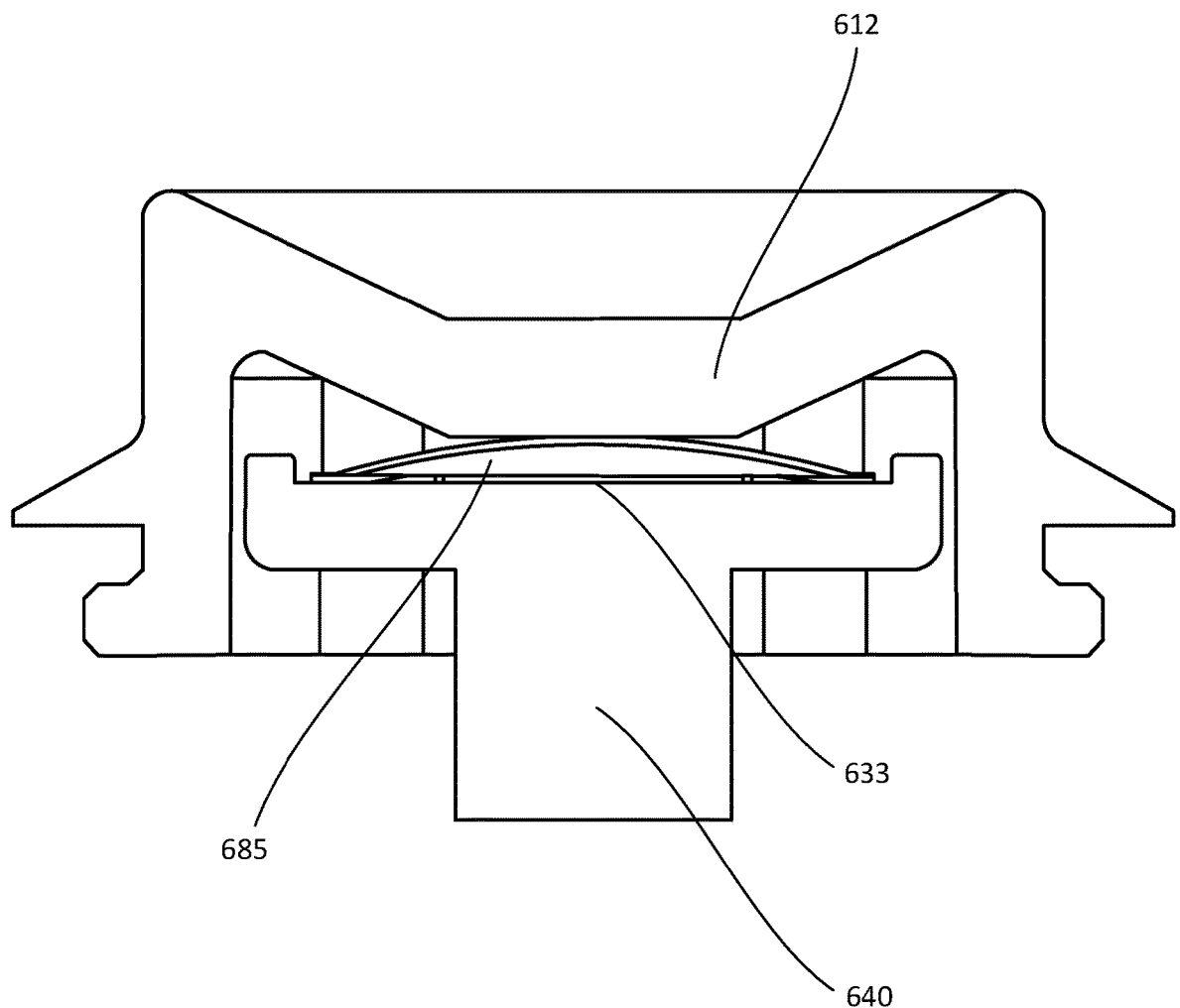
FIG. 6B illustrates the feedback component disposed on an end surface of a movable valve element according to an aspect.

FIGS. 6A through 6B illustrates various perspectives of a feedback component 611 configured to provide at least one of tactile or auditory feedback in response to moving a movable valve element 640 to the deflation position. The feedback component 611 is disposed between the movable valve element 640 and a button component 612. The feedback component 611 may be used in any of the push assemblies discussed herein.

FIG. 6A illustrates the feedback component 611 as a dome structure 685 according to an aspect. In some examples, the dome structure 685 includes a rounded vault and a circular base. In some examples, when the dome structure 685 is compressed, the dome structure 685 may create a sound. In some examples, when the dome structure 685 is compressed, the dome structure 685 may provide a tactile sensation that is perceptible by the user. FIG. 6B illustrates the feedback component 611 disposed on an end surface 633 of the movable valve element 640 according to an aspect. When the button component 612 is pressed, the button component 612 moves the movable valve element 640 in order to place the push valve in the deflation position. The movable valve element 640 and the button component 612 compress the feedback component 611, which causes the feedback component 611 to provide at least one of tactile or auditory feedback.

Figure 7:
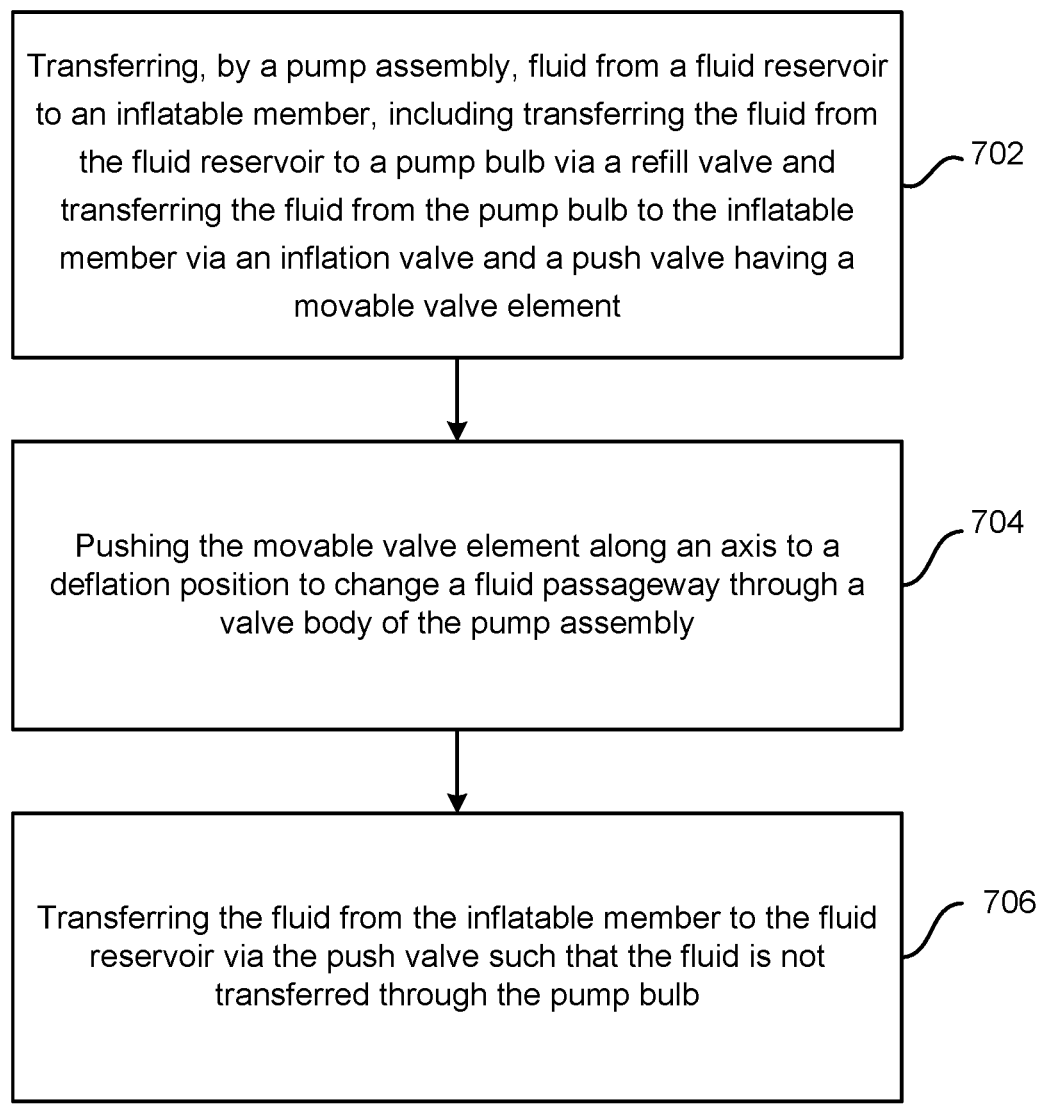
FIG. 7 illustrates a flow chart depicting example operations of a method of controlling a direction of fluid through a pump assembly of an inflatable penile prosthesis according to an aspect.

FIG. 7 illustrates a flow chart 700 depicting example operations of a method of controlling a direction of fluid through a pump assembly of an inflatable penile prosthesis according to an aspect. Although the flow chart 700 is explained with reference to the inflatable penile prosthesis 100 of FIG. 1, the example operations of the flow chart 700 may be performed by any of inflatable penile prostheses, pump assemblies, and/or push valves discussed herein.

Operation 702 includes transferring, by a pump assembly 106, fluid from a fluid reservoir 102 to an inflatable member 104, including transferring the fluid from the fluid reservoir 102 to a pump bulb 108 via a refill valve 120 and transferring the fluid from the pump bulb 108 to the inflatable member 104 via an inflation valve 122 and a push valve 124 having a movable valve element 140. Operation 704 includes pushing the movable valve element 140 along an axis 121 to a deflation position to change a fluid passageway through a valve body 110 of the pump assembly 106. Operation 706 includes transferring the fluid from the inflatable member 104 to the fluid reservoir 102 via the push valve 124 such that the fluid is not transferred through the pump bulb 108.

Figure 8:
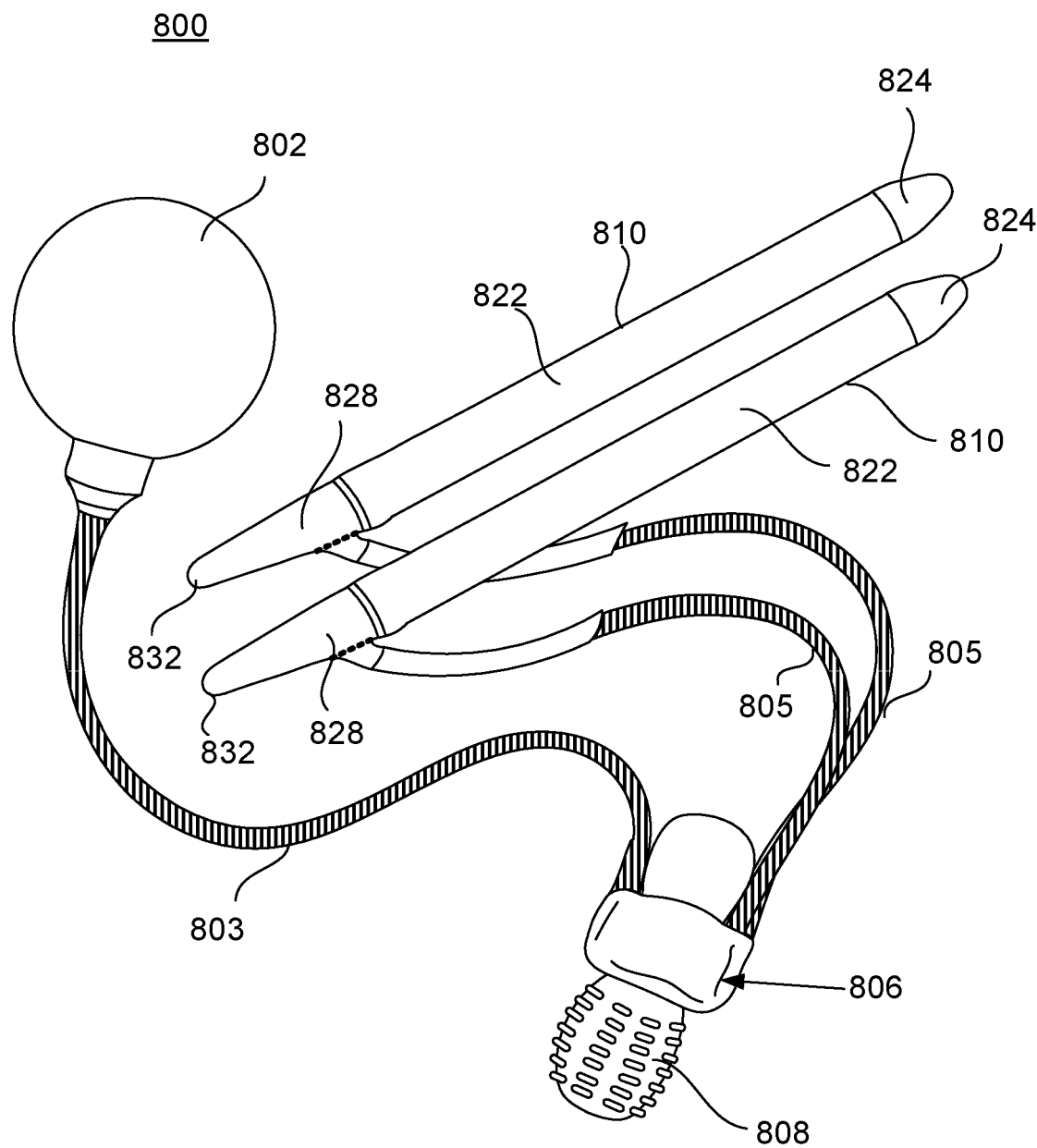
FIG. 8 schematically illustrates an inflatable penile prosthesis having a pump assembly according to an aspect.

FIG. 8 schematically illustrates an inflatable penile prosthesis 800 having a pump assembly 806 according to an aspect. The pump assembly 806 may include any of the features of the pump assemblies (including the push valve) described with reference to the previous figures. The penile prosthesis 800 may include a pair of inflatable cylinders 810, and the inflatable cylinders 810 are configured to be implanted in a penis. For example, one of the inflatable cylinders 810 may be disposed on one side of the penis, and the other inflatable cylinder 810 may be disposed on the other side of the penis. Each inflatable cylinder 810 may include a first end portion 824, a cavity or inflation chamber 822, and a second end portion 828 having a rear tip 832.

The pump assembly 806 may be implanted into the patient's scrotum. A pair of conduit connectors 805 may attach the pump assembly 806 to the inflatable cylinders 810 such that the pump assembly 806 is in fluid communication with the inflatable cylinders 810. Also, the pump assembly 806 may be in fluid communication with a fluid reservoir 802 via a conduit connector 803. The fluid reservoir 802 may be implanted into the user's abdomen. The inflation chamber or portion 822 of the inflatable cylinder 810 may be disposed within the penis. The first end portion 824 of the inflatable cylinder 810 may be at least partially disposed within the crown portion of the penis. The second end portion 828 may be implanted into the patient's pubic region PR with the rear tip 832 proximate the pubic bone PB.

In order to implant the inflatable cylinders 810, the surgeon first prepares the patient. The surgeon often makes an incision in the penoscrotal region, e.g., where the base of the penis meets with the top of the scrotum. From the penoscrotal incision, the surgeon may dilate the patient's corpus cavernosae to prepare the patient to receive the inflatable cylinders 810. The corpus cavernosum is one of two parallel columns of erectile tissue forming the dorsal part of the body of the penis, e.g., two slender columns that extend substantially the length of the penis. The surgeon will also dilate two regions of the pubic area to prepare the patient to receive the second end portion 828. The surgeon may measure the length of the corpora cavernosae from the incision and the dilated region of the pubic area to determine an appropriate size of the inflatable cylinders 810 to implant.

After the patient is prepared, the penile prosthesis 800 is implanted into the patient. The tip of the first end portion 824 of each inflatable cylinder 810 may be attached to a suture. The other end of the suture may be attached to a needle member (e.g., Keith needle). The needle member is inserted into the incision and into the dilated corpus cavernosum. The needle member is then forced through the crown of the penis. The surgeon tugs on the suture to pull the inflatable cylinder 810 into the corpus cavernosum. This is done for each inflatable cylinder 810 of the pair. Once the inflation chamber 822 is in place, the surgeon may remove the suture from the tip. The surgeon then inserts the second end portion 828. The surgeon inserts the rear end of the inflatable cylinder 810 into the incision and forces the second end portion 828 toward the pubic bone PB until each inflatable cylinder 810 is in place.

A pump bulb 808 of the pump assembly 806 may be squeezed or depressed by the user in order to facilitate the transfer of fluid from the fluid reservoir 802 to the inflatable cylinders 810. For example, in the inflation mode, while the user is operating the pump bulb 808, the pump bulb 808 may receive the fluid from the fluid reservoir 802, and then output the fluid to the inflatable cylinders 810. When the user switches to the deflation mode, at least some of the fluid can automatically be transferred back to the fluid reservoir 802 (due to the difference in pressure from the inflatable cylinders 810 to the fluid reservoir 802). Then, the user may squeeze the inflatable cylinders 810 to facilitate the further transfer of fluid through the pump bulb 808 to the fluid reservoir 802.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. An inflatable penile prosthesis comprising:
a fluid reservoir configured to hold fluid;
an inflatable member; and
a pump assembly configured to transfer the fluid between the fluid reservoir and the inflatable member, the pump assembly including a pump bulb, a valve body, a push valve movably coupled to the valve body, a first fluid port configured to be fluidly coupled to the fluid reservoir, and a second fluid port configured to be fluidly coupled to the inflatable member, the push valve including a movable valve element configured to move between an inflation position and a deflation position within a bore of the valve body, the pump assembly including an anti-auto inflate valve disposed fluidically between the bore and the fluid reservoir,
the movable valve element in the inflation position defining a fluid passageway through the bore to transfer fluid from the pump bulb to the second fluid port, the movable valve element, when moved to the deflation position, configured to change the fluid passageway through the bore to transfer fluid from the second fluid port to the first fluid port such that the pump bulb is bypassed.

2. The inflatable penile prosthesis of claim 1, wherein the push valve includes a biasing member that biases the movable valve element to the inflation position.

3. The inflatable penile prosthesis of claim 1, wherein the push valve includes a poppet having a ring member.

4. The inflatable penile prosthesis of claim 1, wherein the movable valve element is configured to move to the deflation position in a linear direction based on a single instantaneous push of the movable valve element by a user.

5. The inflatable penile prosthesis of claim 1, wherein the pump assembly includes a button component that encloses a portion of the movable valve element when the movable valve element is in the inflation position.

6. The inflatable penile prosthesis of claim 5, wherein the pump assembly includes a feedback component disposed between the button component and the movable valve element, the feedback component configured to provide at least one of tactile or auditory feedback in response to the movable valve element being moved to the deflation position.

7. The inflatable penile prosthesis of claim 1, wherein a portion of the movable valve element extends outside the valve body when the movable valve element is in the inflation position, the portion of the movable valve element being disposed inside the valve body when the movable valve element is in the deflation position.

8. The inflatable penile prosthesis of claim 1, wherein the valve body includes a refill valve aligned with the first fluid port, the refill valve configured to transfer fluid from the fluid reservoir to the pump bulb when the movable valve element is in the inflation position.

9. The inflatable penile prosthesis of claim 1, wherein the valve body includes an inflation valve disposed in a fluid passageway between the pump bulb and the bore.

10. The inflatable penile prosthesis of claim 1, wherein the movable valve element includes a first movable member and a second movable member.

11. The inflatable penile prosthesis of claim 1, wherein the valve body includes a refill valve, and an inflation valve, wherein the refill valve and the inflation valve are not used when the movable valve element is in the deflation position.

12. A pump assembly for an inflatable penile prosthesis comprising:
a push valve movably coupled to a valve body, the push valve including a movable valve element configured to move between an inflation position and a deflation position within a bore of the valve body;
a plurality of fluid transfer ports including a first fluid port configured to be fluidly coupled to a fluid reservoir, and a second fluid port configured to be fluidly coupled to an inflatable member; and
an anti-auto inflate valve disposed fluidically between the bore and the fluid reservoir,
the movable valve element in the inflation position defining a fluid passageway through the bore to transfer fluid from a pump bulb to the second fluid port, the movable valve element, when moved to the deflation position, configured to change the fluid passageway through the bore to transfer fluid from the second fluid port to the first fluid port such that the pump bulb is bypassed.

13. The pump assembly of claim 12, wherein the movable valve element includes a cylindrical unitary body having at least two sections with different diameters.

14. The pump assembly of claim 12, wherein the first fluid port includes a first tubular member, and the second fluid port includes a second tubular member and a third tubular member, the second tubular member configured to be fluidly coupled to a first cylinder member of the inflatable member, the third tubular member configured to be fluidly coupled to a second cylinder member of the inflatable member.

15. The pump assembly of claim 12, further comprising:
a refill valve disposed within the valve body at a location that is aligned with a longitudinal axis of the first fluid port; and
an inflation valve disposed in a fluid passageway between the bore and the pump bulb.

16. The pump assembly of claim 12, wherein the movable valve element is configured to move from the inflation position to the deflation position along an axis, the axis being substantially orthogonal to the longitudinal axis of the first fluid port.

17. The pump assembly of claim 12, wherein a portion of the movable valve element extends outside the valve body when the movable valve element is in the inflation position, the pump assembly further comprising:
a button component that encloses the portion of the movable valve element; and
a feedback component disposed between the button component and an end portion of the movable valve element, the feedback component configured to provide at least one of tactile or auditory feedback in response to the movable valve element being moved to the deflation position.

18. A method for controlling a direction of fluid through a pump assembly of an inflatable penile prosthesis, the method comprising:
transferring, by a pump assembly, fluid from a fluid reservoir to an inflatable member, including:
transferring the fluid from the fluid reservoir to a pump bulb via a refill valve;
transferring the fluid from the pump bulb to the inflatable member via an inflation valve and a push valve having a movable valve element;
pushing the movable valve element disposed within a bore along an axis to a deflation position to change a fluid passageway through a valve body of the pump assembly; and
transferring the fluid from the inflatable member to the fluid reservoir via the push valve such that the fluid is transferred through the bore and an anti-auto inflate valve disposed fluidically between the bore and the fluid reservoir and such that the fluid is not transferred through the pump bulb.

19. The method of claim 18, wherein the refill valve and the inflation valve are not used to transfer the fluid from the inflation member to the fluid reservoir when the movable valve element is in the deflation position.

20. The inflatable penile prosthesis of claim 1, wherein the anti-auto inflate valve includes a check ball and a biasing member.

* * * * *